US009492300B2

(12) United States Patent
Bujold et al.

(10) Patent No.: US 9,492,300 B2
(45) Date of Patent: Nov. 15, 2016

(54) EXOSKELETON AND METHOD OF USING THE SAME

(71) Applicant: Mawashi Protective Clothing Inc, St-Jean-sur-Richelieu, Quebec (CA)

(72) Inventors: Alain Bujold, St-Jean-sur-Richelieu (CA); Jean-Marc Sheitoyan, St-Jean-sur-Richelieu (CA); Francois Tremblay, Saint-Eustache (CA); Patrice Paquette, Melbourne (CA); Aleksander Pohl, Lachine (CA); Simon Forget, Laval (CA); Anis Ouanes, Longueuil (CA); Alain Vary, Waterloo (CA)

(73) Assignee: Mawashi Protective Clothing Inc., Saint-Jean-sur-Richelieu, Quebec (CA)

( * ) Notice: Subject to any disclaimer, the term of this patent is extended or adjusted under 35 U.S.C. 154(b) by 11 days.

(21) Appl. No.: 14/743,102

(22) Filed: Jun. 18, 2015

(65) Prior Publication Data

US 2015/0366694 A1 Dec. 24, 2015

Related U.S. Application Data

(60) Provisional application No. 62/013,722, filed on Jun. 18, 2014.

(51) Int. Cl.
*A61F 5/00* (2006.01)
*A61F 5/01* (2006.01)
*A61F 5/02* (2006.01)

(52) U.S. Cl.
CPC ............. *A61F 5/0102* (2013.01); *A61F 5/028* (2013.01)

(58) Field of Classification Search
CPC ................... A61F 2002/701; A61F 2002/704; A61F 2002/7625; A61F 2002/7645; A61F 2/68; A61F 2002/7635; A61F 5/0102; A61F 2/60; A61F 2/6607; A61F 2002/503; A61F 2002/5003; A61F 2002/764; A61F 5/01; A61F 2002/5007; A61F 2002/50

USPC ....................................... 602/16, 19; 623/27
See application file for complete search history.

(56) References Cited

U.S. PATENT DOCUMENTS 8,474,672 B1   7/2013 Keith
2011/0264014 A1  10/2011 Angold
(Continued)

FOREIGN PATENT DOCUMENTS

| CA | 2724062 | 2/2010 |
|---|---|---|
| CA | 2746327 | 9/2010 |
| WO | 2014159608 | 10/2014 |

OTHER PUBLICATIONS

International Search Report PCT/ISA/210 of PCT/CA2015/050559.
(Continued)

*Primary Examiner* — Michael Brown
(74) *Attorney, Agent, or Firm* — Damien Calvet; Brouillette & Partners

(57) ABSTRACT

An exoskeleton designed to be worn by a user is generally configured to support and transfer the load supported by the head, the neck and/or the torso (shoulders, chest and/or back) of the user down to the ground. The exoskeleton is generally passive and comprises at least three interconnected sections: torso, hip, and leg sections. Each of the sections generally comprises of a plurality of interconnected rigid members which form the load-bearing structure of the exoskeleton. When a user wears the exoskeleton, load normally carried by the head, neck and/or torso of the user is at least partially supported and transferred to the ground by the exoskeleton, thereby reducing the load effectively supported by the user itself. The leg sections of the exoskeleton are designed to ensure that the load-bearing final location is located on the inner side of the feet, in accordance with human biomechanics.

20 Claims, 22 Drawing Sheets

(56) References Cited

U.S. PATENT DOCUMENTS

| | | | |
|---|---|---|---|
| 2012/0172770 A1* | 7/2012 | Almesfer et al. | B25J 9/0006 601/35 |
| 2013/0226048 A1* | 8/2013 | Unluhisarcikli et al. | A61H 3/00 601/34 |
| 2013/0303950 A1* | 11/2013 | Angold et al. | B25J 9/0006 601/35 |
| 2015/0001269 A1* | 1/2015 | Sacksteder | F16M 13/04 224/576 |

OTHER PUBLICATIONS

Written Opinion PCT/ISA/237 of PCT/CA2015/050559.

* cited by examiner

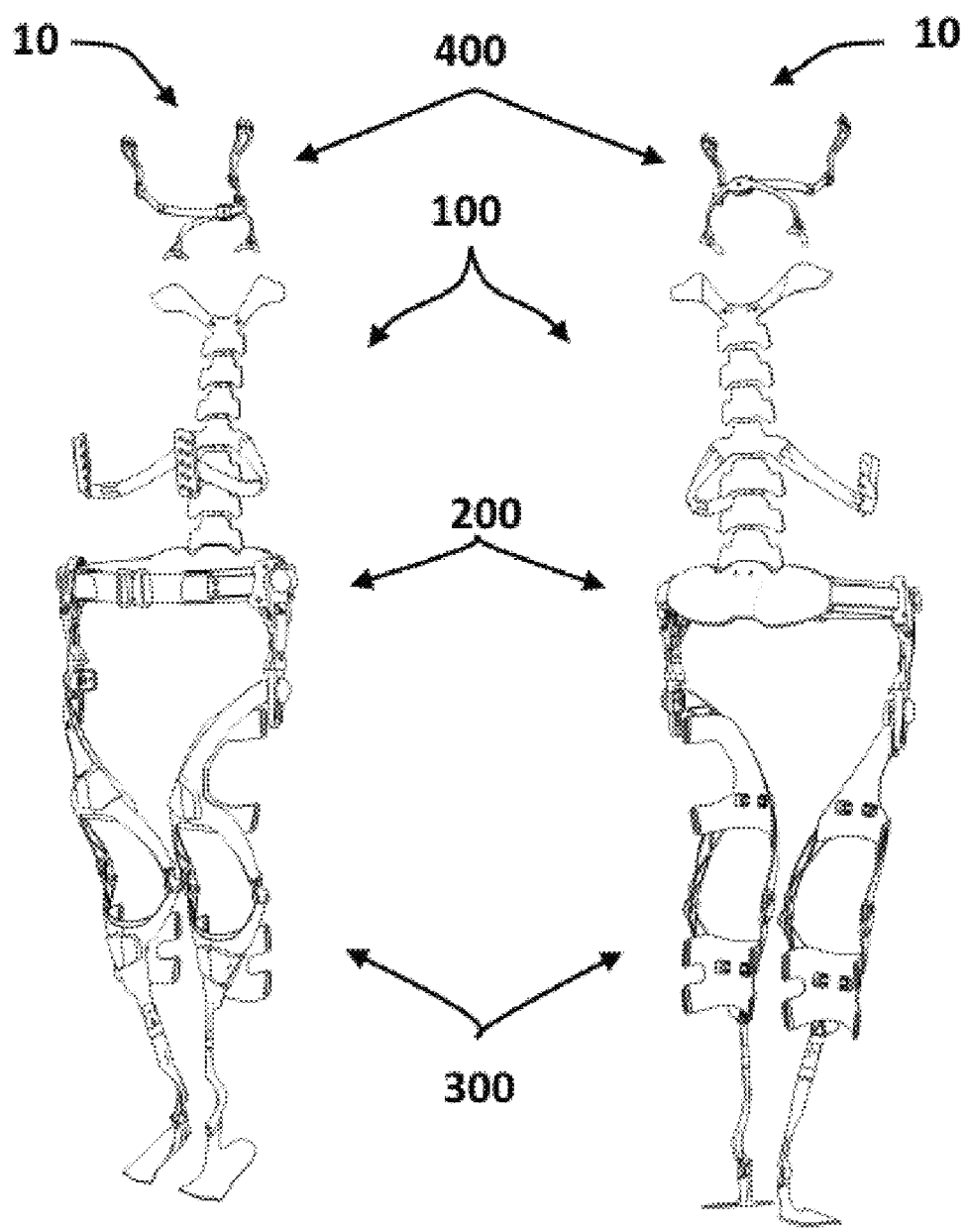

EXOSKELETON AND METHOD OF USING THE SAME

CROSS-REFERENCE TO RELATED APPLICATIONS

The present patent application claims the benefits of priority of U.S. Patent Application No. 62/013,722, entitled "Passive Exoskeleton and Method of Using the Same", and filed at the United States Patent and Trademark Office on Jun. 18, 2014, the content of which is incorporated herein by reference.

FIELD OF THE INVENTION

The present invention generally relates to exoskeletons and other wearable structures configured to assist humans in carrying loads, and more particularly relates to passive and/or non-powered exoskeletons and other passive and/or non-powered wearable structures configured to assist humans in carrying loads.

BACKGROUND OF THE INVENTION

Helping users carrying heavy loads has long been a need in many circumstances. For example, soldiers in the field, firefighters, police officers, antiriot squads, but also construction workers, and hikers, are often faced with the problem of carrying heavy loads, sometimes over long distances. Solutions to such a problem that have been proposed over the years, have sometimes taken the form of a portable structure, also known as an exoskeleton, to be worn by the user, sometimes as a complement to the legs, sometimes through the legs and torso.

U.S. Pat. No. 8,474,672 by Keith teaches an arrangement for replaceably supporting a backpack having a load on the back of the user and transferring the load of the backpack to the ground by way of the legs of the user while allowing the user to take steps unhindered. However, such arrangement does not allow for flexibility of the legs, when the user often needs to be able to squat.

Most of the solutions proposed are powered, i.e. comprise motor driven mechanism for helping the carrying of the load. For example, U.S. Patent Application No. 2011/0264014 (Angold et al.) teaches a portable load lifting system.

Other prior art provides extension frames which extend from an exoskeleton trunk and are configured to hold a load in front of a person wearing the exoskeleton, as taught by U.S. Pat. No. 8,057,410 B2 (Angold et al.). While useful, such a configuration does not provide for easy manipulation of a load by the wearer over a long distance. Additionally, such a device does not address the problem of unequal weight distribution about an exoskeleton trunk, which could cause significant balancing problems for a wearer of the exoskeleton, while the wearer is stationary as well as walking.

Therefore, most of the prior art consists of powered exoskeletons, which, although useful in certain circumstances, may be inadequate, due to the excess weight, costs, dependence on power supply, and lack of ergonomic mobility for the user.

Furthermore, most of the prior art consists of exoskeletons which have their load bearing design directed on the outside of the leg, which is not compatible with the human biomechanics and which may cause serious injuries to the user. See for instance U.S. Pat. No. 8,474,672 B1 (Keith) and U.S. Pat. No. 8,968,222 B2 (Kazerooni et al.), or U.S. patent application No. US 2013/0303950 A1 (Angold et al.).

Therefore, despite ongoing developments in the field of load-carrying exoskeletons, there is a need for novel biomimetic non-powered load-carrying exoskeletons that can mitigate some of the shortcomings of the prior art.

SUMMARY OF THE INVENTION

The shortcomings of prior art exoskeletons are at least mitigated by an exoskeleton, such as a passive exoskeleton, which is configured to be worn by a user such as to support and transfer load normally carried by the user down to the ground, thereby reducing the load support by the user itself.

The invention is first directed to an exoskeleton configured to be worn by a user to support and transfer a load carried by the user down to the ground; the exoskeleton comprising a torso section connected to a leg section via a hip section such as to transfer the load carried by the torso section down to the ground via the hip section and then the leg section; wherein the leg section comprises two symmetrical articulated leg assemblies, each leg assembly being adapted to be maintained on each user's leg and to follow the leg's movements when the exoskeleton is in use, each leg assembly having an upper end operatively connected to an outer side of the hip section and a bottom end adapted to be in contact with the ground, each leg assembly being configured to transfer the load from the outer side of the hip section to an inner side of the user's leg before connecting to the ground.

According to another embodiment, the present invention is directed to an exoskeleton configured to be worn by a user. The exoskeleton comprises a torso section connected to a leg section via a hip section such as to support and transfer a load carried by the torso section down to the ground via the hip section and then the leg section. The leg section comprises two symmetrical articulated leg assemblies, each leg assembly being adapted to be maintained on each user's leg and to follow the leg's movements when the exoskeleton is in use. Each leg assembly have an upper end operatively connected to an outer side of the hip section and a bottom end adapted to be in contact with the ground, each leg assembly being configured to transfer the load from the outer side of the hip section to an inner side of the user's leg before contacting the ground. Each leg assembly comprises an upper leg member extending downwardly from the hip section and having an end pivotally connected to the hip section to allow the upper leg member to move with respect to the hip section when the user moves. The lower leg member extends downwardly from the upper leg member and pivotally connected to the upper leg member, the pivotal connection between the upper and lower leg members being located at a knee level of the user to allow the lower leg member to follow the movements of the lower leg of the user with respect to the upper leg. The upper and lower leg members extend downwardly and toward the inner side of the user's leg such as to transfer the load from the outside of the leg toward the inside of the leg and down on the inner side of the foot of the user. The upper leg member comprises an upper region extending downwardly from the outer side of the hip section toward a front of the leg, and then extending downwardly from the upper region to a lower region terminated near the knee level by two extremities as the lower region splits on each side of the leg. The lower leg member comprises an upper region pivotally extending from the lower region of the upper leg member and a lower region extending downwardly therefrom toward the inner side of the user's leg. Finally, the upper region of the lower member also splits in two extremities which are each pivotally connected to the two extremities of the lower region of the upper leg member defining as such a central opening to allow the knee of the user to extend through said opening when the user kneels or squats; the pivotal connection between the said extremities being aligned with the knee of the user in order to allow the leg of the user to bend along the knee.

According to another embodiment, the present invention is directed to an exoskeleton configured to be worn by a user. The exoskeleton comprises a torso section connected to a leg section via a hip section such as to support and transfer a load carried by the torso section down to the ground via the hip section and then the leg section. The leg section comprises two symmetrical articulated leg assemblies, each leg assembly being adapted to be maintained on each user's leg and to follow the leg's movements when the exoskeleton is in use. Each leg assembly has an upper end operatively connected to an outer side of the hip section and a bottom end adapted to be in contact with the ground. Each leg assembly is configured to transfer the load from the outer side of the hip section to an inner side of the user's leg before contacting the ground. The torso section of the exoskeleton comprises a shoulder member configured to rest on the shoulders of the user; and a spine assembly extending downwardly from the shoulder member along the user's spine. The spine assembly comprises a plurality of spinal members wherein an uppermost spinal member is connected to, or integral with, the shoulder member, while a lowermost spinal member is connected to the hip section. Each leg assembly comprises an upper leg member extending downwardly from the hip section and having an end pivotally connected to the hip section to allow the upper leg member to move with respect to the hip section when the user moves; and a lower leg member extending downwardly from the upper leg member and pivotally connected to the upper leg member. The pivotal connection between the upper and lower leg members is located at a knee level of the user to allow the lower leg member to follow the movements of the lower leg of the user with respect to the upper leg. Finally, the upper and lower leg members extend downwardly and toward the inner side of the user's leg such as to transfer the load from the outside of the leg toward the inside of the leg and down on the inner side of the foot of the user.

The invention is also directed to a method for supporting and transferring a load carried down to the ground, the method comprising the steps of:
  wearing the exoskeleton as described herein;
  providing at least one load; and
  carrying the at least one load using the torso section of the exoskeleton for transferring the at least one load from the outer side of the hip section to an inner side of the leg section before connecting the leg section to the ground.

The invention is also directed to a method for supporting and transferring a load carried down to the ground, the method comprising the steps of:
  wearing an exoskeleton comprising a torso section downwardly connected to a leg section via a hip section; and
  transferring the load carried by the torso section of the exoskeleton from the outer side of the hip section to an inner side of the leg section before connecting the leg section to the ground.

In use, a user will wear the exoskeleton to assist it in carrying loads. As a load is applied to the torso of the user, the load will at least be partially supported by the torso section and will be transferred down to the hip section via the torso section and its connection with the hip section. The hip section will then further transfer the load down to the leg section. Finally, the load will be transferred to the ground via the leg section. In that sense, the final left and right load-bearing contact points are located on the inner the side of the left and right feet.

To allow a load transfer more aligned with human biomechanics, the leg sections of the exoskeleton are generally connected to the sides of the hip section but are configured to transfer the load on the inner side of the feet. Accordingly, the transfer of the load from the outside of the hip down to the inside of the legs advantageously ease the movements of the user wearing the exoskeleton, even when carrying important loads, extending as such the distance and/or time the user will carried the loads.

Though various users could use an exoskeleton in accordance with the principles of the present invention, such an exoskeleton can be advantageously worn by soldiers, police officers (including antiriot and SWAT team personnel), firefighters, construction workers, camera operators, and hikers to assist them in carrying loads.

Other and further aspects and advantages of the present invention will be better understood with the illustrative embodiments about to be described or indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which:

FIG. 1 is a front perspective view of an embodiment of an exoskeleton in accordance with the principles of the present invention.

FIG. 2 is a rear perspective view of the exoskeleton of FIG. 1.

DETAILED DESCRIPTION OF PREFERRED EMBODIMENTS

Figures 3, 4:
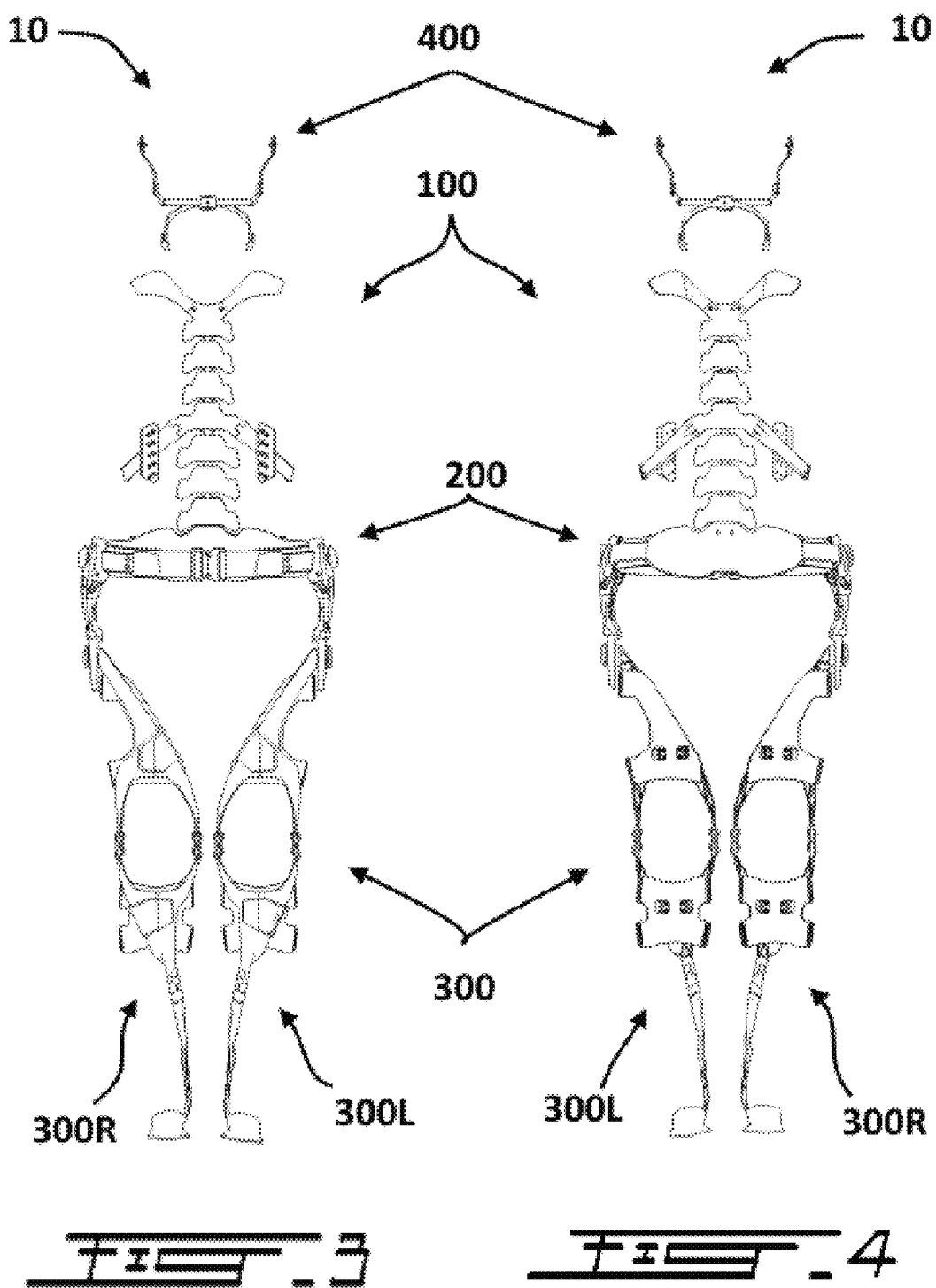
FIG. 3 is a front view of the exoskeleton of FIG. 1.
FIG. 4 is a rear view of the exoskeleton of FIG. 1.
Figures 5, 6:
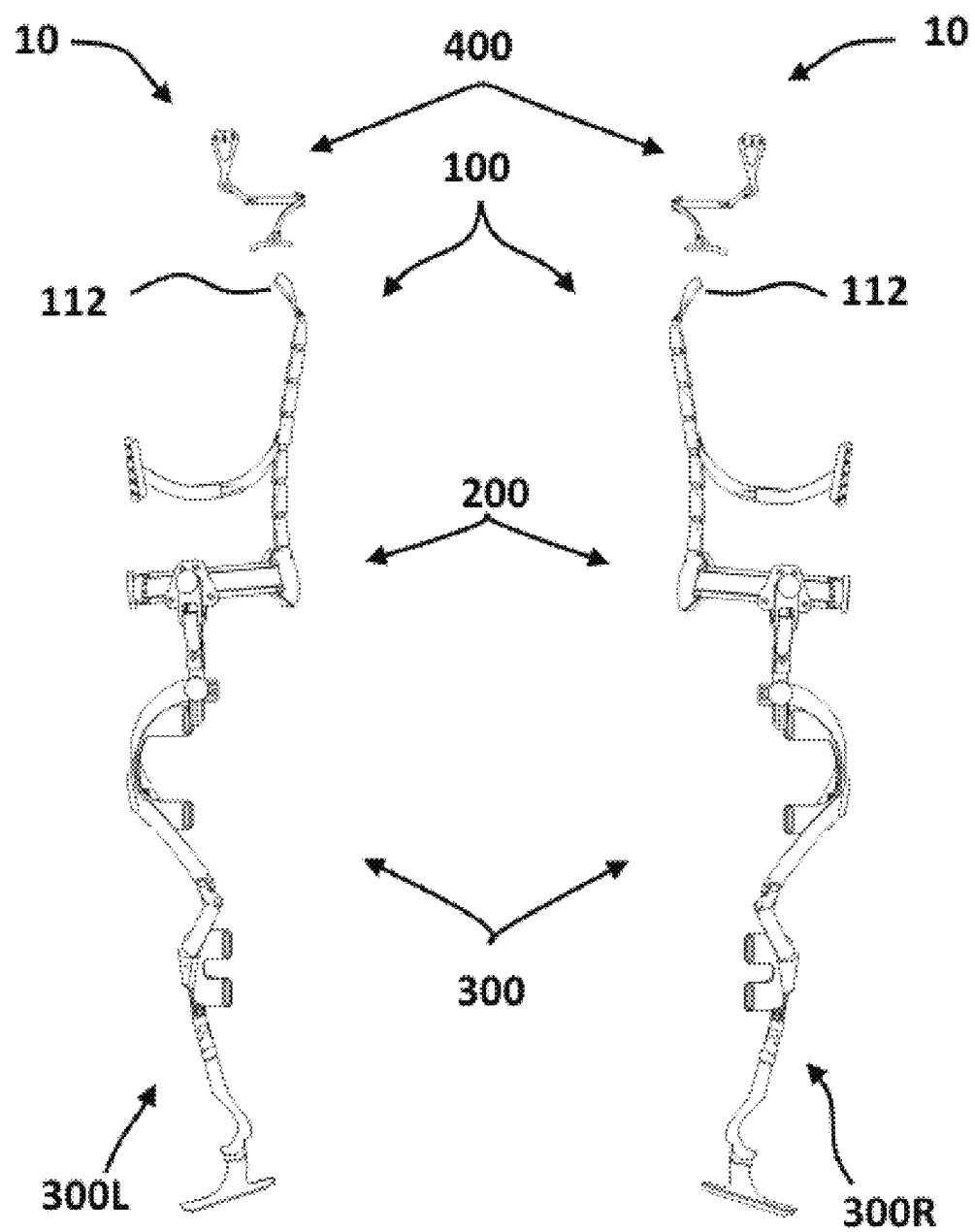
FIG. 5 is a left side view of the exoskeleton of FIG. 1.
FIG. 6 is a right side view of the exoskeleton of FIG. 1.

A novel load carriage exoskeleton will be described hereinafter. Although the invention is described in terms of specific illustrative embodiments, it is to be understood that the embodiments described herein are by way of example only and that the scope of the invention is not intended to be limited thereby.

An exoskeleton in accordance with the principles of the present invention generally comprises at least three interconnected sections, 1) a torso section, 2) a hip section, and 3) leg sections. These three sections are interconnected such as to transfer the load normally carried by the torso, including the shoulders, chest, and back of the user, down to the ground via the hip section and then the leg sections.

To allow a load transfer which is more aligned with human biomechanics, the leg sections of the exoskeleton are generally connected to the sides of the hip section but are configured to transfer the load on the inner side of the feet.

In typical embodiments, the torso section of the exoskeleton generally comprises a shoulder member configured to rest on the shoulders of the user, and a spine assembly comprising a plurality of spinal members. The uppermost spinal member is connected to, or integral with, the shoulder member, while the lowermost spinal member is connected to the hip section. The shoulder and spinal members are interconnected by resilient members (e.g. springs) to allow the spine assembly to compress or extend under load and to allow the spine assembly to relatively follow the movements of the user. The torso section generally supports and transfers load normally carried by the shoulders and torso of the user toward the ground via the hip section and then the leg sections.

In some embodiments, the torso section also comprises at least one pair of left and right rib members which extend on each side of at least one intermediate spinal member all the way to the front of the torso of the user, generally at the level of the lowest ribs, between the thorax and abdomen. When present, these rib members effectively support and transfer load normally carried by the thorax or abdomen toward the spinal assembly and then toward the ground via the hip and leg sections.

In typical embodiments, the hip section of the exoskeleton generally comprises a lower back member and left and right hip members extending from each side of the lower back member all the way to the front of the user. The lower back member receives the lowest extremity of the spine assembly of the torso section. The free extremities of the left and right hip members are provided with complementary fasteners such as to be attachable together to form a belt. For added comfort, the inner surface of the lower back and hip members are typically lined with resilient material such as elastomeric foam.

In typical embodiments, the leg sections of the exoskeleton comprise a left leg section and a right leg section. The left and right leg sections are generally symmetrical. The left leg section is mounted to the left hip member of the hip section while the right leg section is mounted to the right hip member of the hip section.

Each leg section generally comprises three main portions, a hip joint assembly, an upper leg member and a lower leg member. The hip joint assembly is mounted to the appropriate hip member of the hip section and to the upper extremity of upper leg member. The hip joint assembly is articulated to allow the upper leg member to move with respect to the hip section when the user moves (e.g. walking, running, kneeling, squatting, etc.). The upper leg member is connected to the hip joint assembly, and to the lower leg member. The upper extremity of the upper leg member is pivotally mounted to the hip joint assembly, and the lower extremity of the upper leg member is pivotally connected to the lower leg member. The pivotal connection between the upper and lower leg members is generally located at the knee level of the user to allow the lower leg member to follow the movements of the lower leg of the user with respect to the upper leg. The lower leg member generally extends downwardly and toward the inner side of the leg of the user such as to transfer the load from the outside of the leg toward the inside of the leg and down on the inner side of the foot of the user. In that sense, the lower extremity of the lower leg member is terminated with a sole insert configured to be received in the footwear (e.g. boot) of the user.

In some embodiments, the exoskeleton also comprises a neck section (a fourth section). The neck section is configured to assist in supporting load carried by the head of the user. The neck section is generally connected, directly or via a protective vest or suit, to the torso section such as to transfer the load from the head and neck of the user toward the torso section which will further transfer the load down via the hip and leg sections.

In use, a user will wear the exoskeleton to assist it in carrying loads. As a load is applied to the torso (e.g. shoulder, chest and/or back) of the user, the load will at least be partially supported by the torso section (e.g. shoulder member, spine assembly) and will be transferred down to the hip section via the spine assembly and its connection with the hip section. The hip section will then further transfer the load down to the two leg sections via the connection between the left hip member and the left leg section, and via the connection between the right hip member and the right leg section. Finally, the load will be transferred to the ground via the left and right sole inserts located in the footwear of the user. In that sense, as mentioned above, the final left and right load-bearing contact points are located on the inner the side of the left and right feet.

According to one aspect of the present invention, the exoskeleton may comprise a plurality of subsystems:

Sub-System 1: Lower Limbs

Sole: embedded directly inside the sole of the soldier's boot, this metallic sole is the foundation, the siege of the balance and equilibrium necessary for this device to properly transfer and redirect the load from the whole body to the floor.

Foot extension mechanism: this is the junction between the foot and the lower side of the tibia.

Outside Medial Malleus connector: this area of the device is specifically designed to ensure proper transfer of the load above without impeding donning/doffing of the boots.

Inside Medial Malleus connector: this area of the device is specifically designed to ensure proper transfer of the load above without impeding donning/doffing of the boots.

Tibia-Knee extension mechanism: this is the lower area of the knee as a continuation of the tibia.

Front-Tibia Extender mechanism: this area opens up just in front of the tibia to allow proper transfer of the redirected load coming from above.

Back-Tibia Connector mechanism: this area allows proper attachment of the device to the back of the tibia.

Front-Hip Extender mechanism: this area opens up just in front of the hip to allow proper transfer of the redirected load coming from above.

Back-Thigh Connector mechanism: this area allows proper attachment of the device to the back of the hip.

Belt-Thigh Junction Pivot: this junction mechanism allows proper movement of the hip/thigh area while ensuring proper load transfer.

Thigh abduction Extender: this area makes the bridge between the upper body loads transferred below via the belt system.

Sub-System 2: Belt

Belt-Thigh Junction Connector: this area allows proper attachment of the device to the back of the tibia.

Belt Track mechanism: this area allows proper attachment of the device to the back of the tibia.

Sub-System 3: Upper Body

Load-Lifter Wings: this part lifts the weight away from the shoulders torso so as to free the body from this load which will be redirected to the floor via the transfer mechanisms.

Vertebrae: this part acts like a human spine allowing proper mobility of the upper torso before connecting to the belt for transmission of the load coming from above.

Vertebrae-Ribs: This is a special vertebrae, unlike the others (o), which extends/grow two floating ribs that will embrace the torso from back to front.

Rib-plate Connector: This part located at the extremity of the floating rib helps avoid compression of the torso by slightly pushing the tight ballistic vest away.

Rib Adjustment Track: This is the mechanism that allows proper adjustment and fixation of this entire sub-system of the exoskeleton on the torso.

Sub-System 4: Upper Shoulder

Upper-Ear Pivot Branch: This is the highest part of the upper shoulder sub-system which is connected to the helmet. This sub-system utilizes an Assisted Torque System (ATS) to literally assist and control the motion of the neck while transferring a portion of the weight of the helmet to the sub-system below via the Lifter Wings (n).

Lower-Ear Pivot Branch: This is part of the upper shoulder sub-system, with the same function as (s).

Neck Rail Slider: This mechanism allows adjustment of the position of the helmet on the upper shoulder sub-system for proper load balancing and movement control/assistance of the neck.

Neck Pivot Branch: This mechanism is also part of the upper shoulder sub-system designed to function as described in (s). It mainly concerns the movement of the neck.

An exoskeleton in accordance with the principles of the present invention is generally shown at 10 in FIGS. 1 and 2. The exoskeleton 10 is designed to allow a user, carrying a load on its torso, to have the exoskeleton 10 take the load from the torso by lifting it away from the body of the user and have it redirected to the ground underneath the foot while the user is standing, walking, running, or squatting. In the present embodiment, the exoskeleton 10 is also configured to at least partially support the weight of a helmet that the user might be wearing.

Referring now to FIGS. 1 to 6, the exoskeleton 10 generally comprises three main sections, 1) a torso section 100, 2) a hip section 200, and 3) leg sections 300L and 300R. These three sections 100, 200 and 300 are interconnected such as to transfer the load normally carried by the torso, including the shoulders, chest, and back of the user, down to the ground via the torso section 100, the hip section 200 and then the leg sections 300L and 300R. In some embodiments, as it will be explained below, the exoskeleton 10 may further comprise a neck section 400.

Understandably, the torso section 100, the hip section 200 and the leg sections 300L and 300R are generally respectively configured to be mounted to the torso, around the hips and on the legs of the user. In that sense, the torso section 100, the hip section 200 and the leg sections 300L and 300R are generally all provided with various adjustment mechanisms (e.g. straps, lateral and longitudinal adjustments on the hips (1 inch), on the ankle (half an inch), and on the spine (4 inches), as well as mechanical fittings, bolts, screws and nuts) to properly adjust the various sections 100, 200, 300L and 300R to the particular size and shape of the body of the user. In the present embodiments, the adjustment mechanisms include crossing straps to facilitate the expansion of the muscles. According to one embodiment, the load carriage exoskeleton, although allowing a degree of adjustability, may be made in different sizes to fit various kind of body sizes and types.

Figure 7:
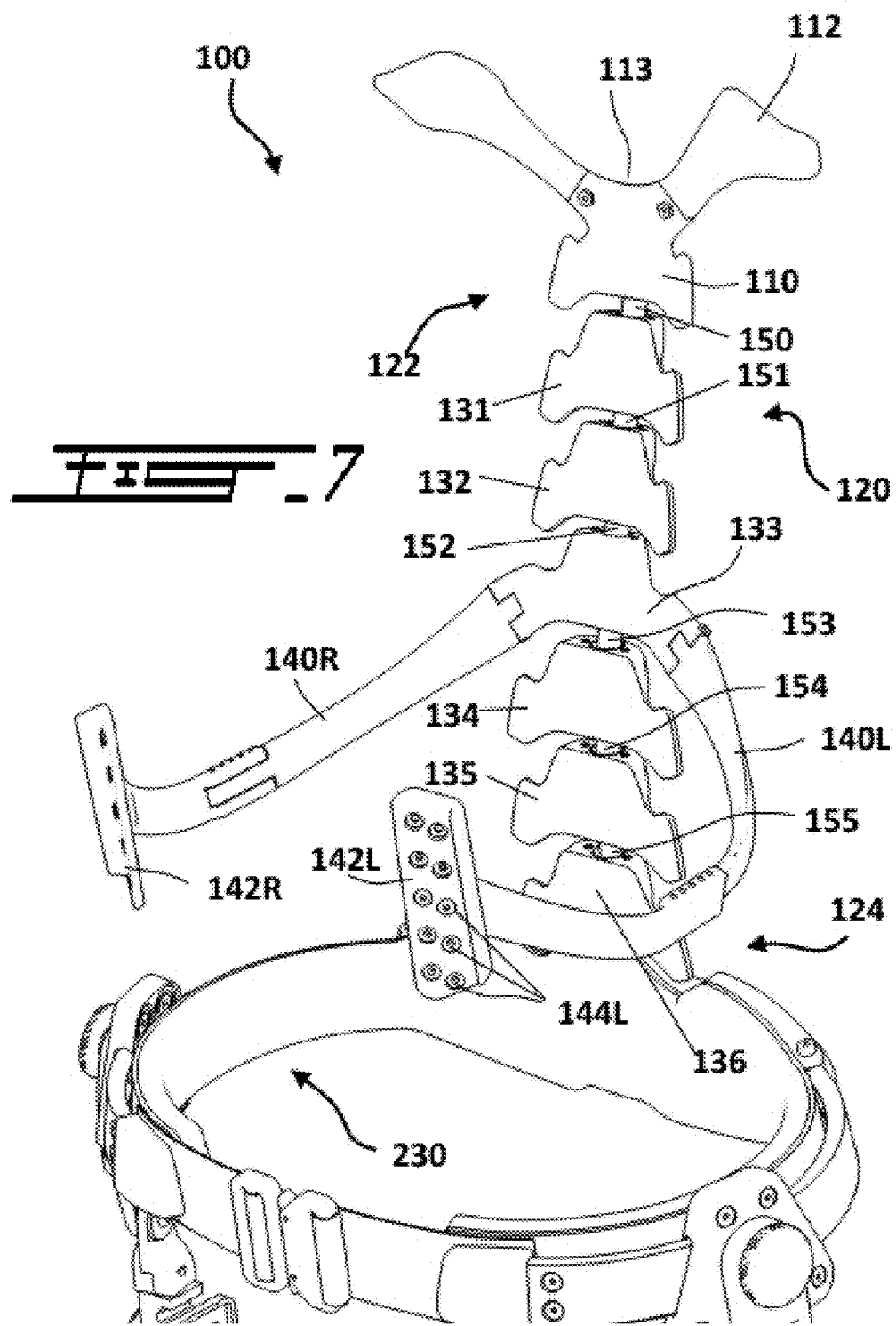
FIG. 7 is a front perspective view of the torso section of the exoskeleton of FIG. 1.
Figure 8:
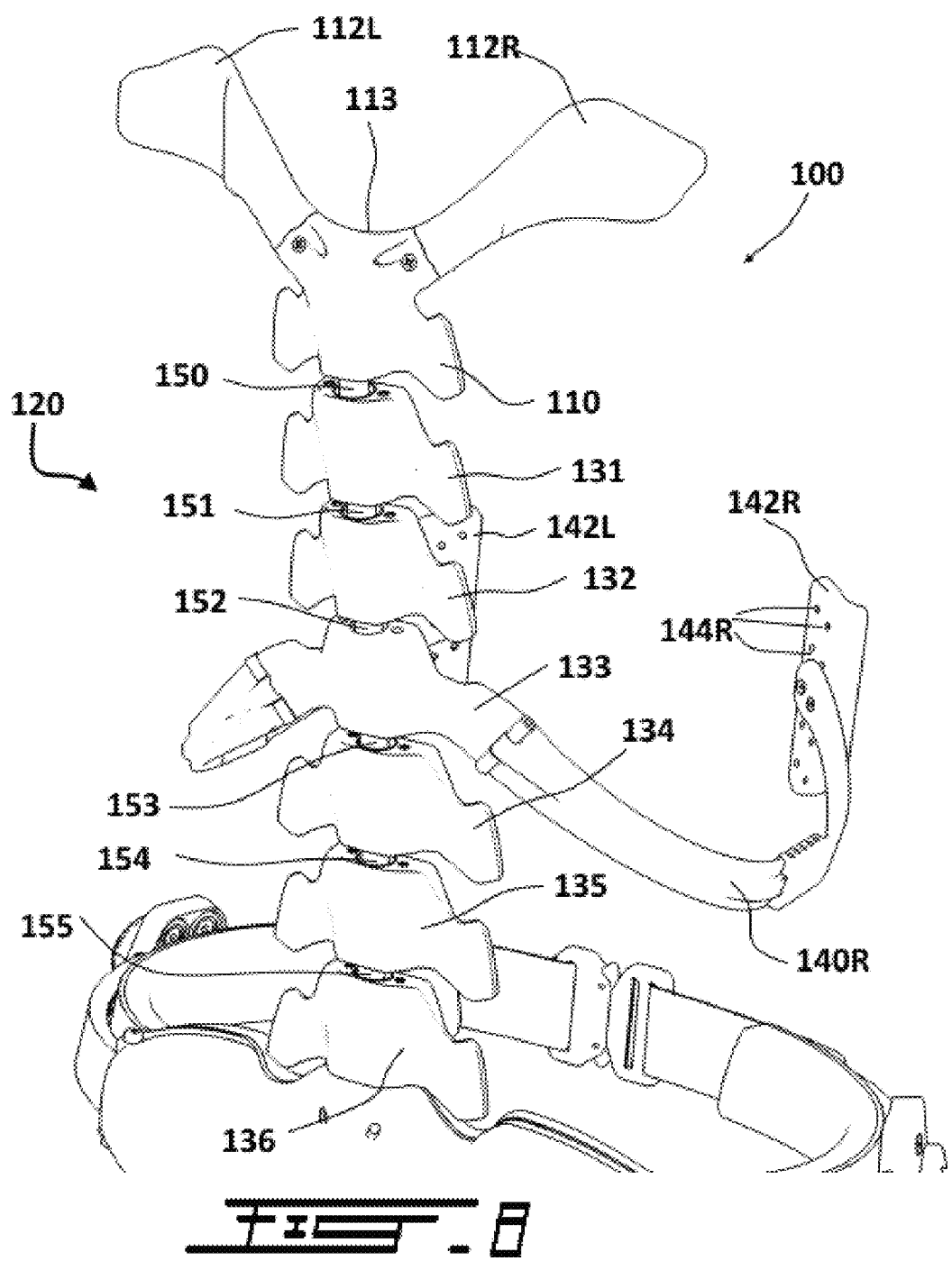
FIG. 8 is a rear perspective view of the torso section of the exoskeleton of FIG. 1.

With additional reference to FIGS. 7 and 8, the torso section 100 may comprise a shoulder member 110 and a spine assembly 120. As shown in FIG. 7, the shoulder member 110 is located at the upper extremity 122 of the spine assembly 120. The shoulder member 110 is generally configured to take at least a portion of the load applied on the torso of the user and transfer it to the spine assembly 120 which will further transfer the load down via the hip section 200 and to the leg sections 300L and 300R.

As best shown in FIGS. 7 and 8, in the present embodiment, the shoulder member 110 is generally configured to partially surround the base of the neck of the user. In that sense, the shoulder member 110 comprises two wing-shaped extensions 112L and 112R which define a recess 113 where the base of the neck of the user can be located.

The spine assembly 120, which is similar to a human spine, generally comprises a plurality of interconnected spinal members or vertebrae 131 to 136. In the present embodiment, the spine assembly 120 comprises 6 individual spinal members. However, in other embodiments, the number of spinal members could be more or less than 6.

The shoulder member 110 and the spinal members 131 to 136 are interconnected with resilient members (e.g. springs) 150 to 155 in order for the spine assembly 120 to compress and extend under the different load it supports and transfers. The resilient interconnection between the shoulder member 110 and the spinal members 131 to 136 also gives flexibility to the torso section 100 of the exoskeleton 10. Since the exoskeleton 10 is configured to be worn by a user, it may be advantageous that the exoskeleton 10 be able to follow the movements of the user while maintaining its load-bearing capabilities. In the present embodiment, the resilient interconnection between the shoulder member 110 and the spinal members 131 to 136 allows the torso section 100 to support at least part of the load applied to the torso of the user while remaining flexible enough to follow most of the movements of the user.

In the present embodiment, at least one of the spinal members 131 to 136 further comprises at least one pair of left and right rib members 140L and 140R which extend on each side of at least one intermediate spinal member all the way to the front of the torso of the user, generally at the level of the lowest ribs, between the thorax and abdomen. In the present embodiment, as best shown in FIGS. 7 and 8, only spinal member 133 comprises rib members 140L and 140R. Rib members 140L and 140R are configured to at least partially support a load which would be localized on the thorax and/or abdomen of the user and to transfer it to the spine assembly 120. In that sense, in the present embodiment, rib members 140L and 140R are respectively terminated by adjustable mounting plates 142L and 142L to which the load could be mounted or attached. In the present embodiment, the mounting plates 142L and 142R are provided with an array of fastener openings 144L and 144R to provide different adjustment for the mounted or attached load. In a military setting, rib members 140L and 140R and their respective mounting plates 142L and 142R could be used, for example, to at least partially support ballistic plates used for protecting soldiers from high velocity bullets and other shrapnel.

Understandably, depending the intended use of the exoskeleton 10, more spinal members could be provided with rib members (if the user has to carry large front load, e.g. a camera operator) or be devoid of rib members altogether (if the user doesn't have to carry large front load, e.g. a hiker).

By virtue of its configuration, the torso section 100 will at least partially support a load carried by the torso of the user and transfer it down to the hip section 200 which will further transfer it to the ground via the leg sections 300L and 300R.

Figure 9:
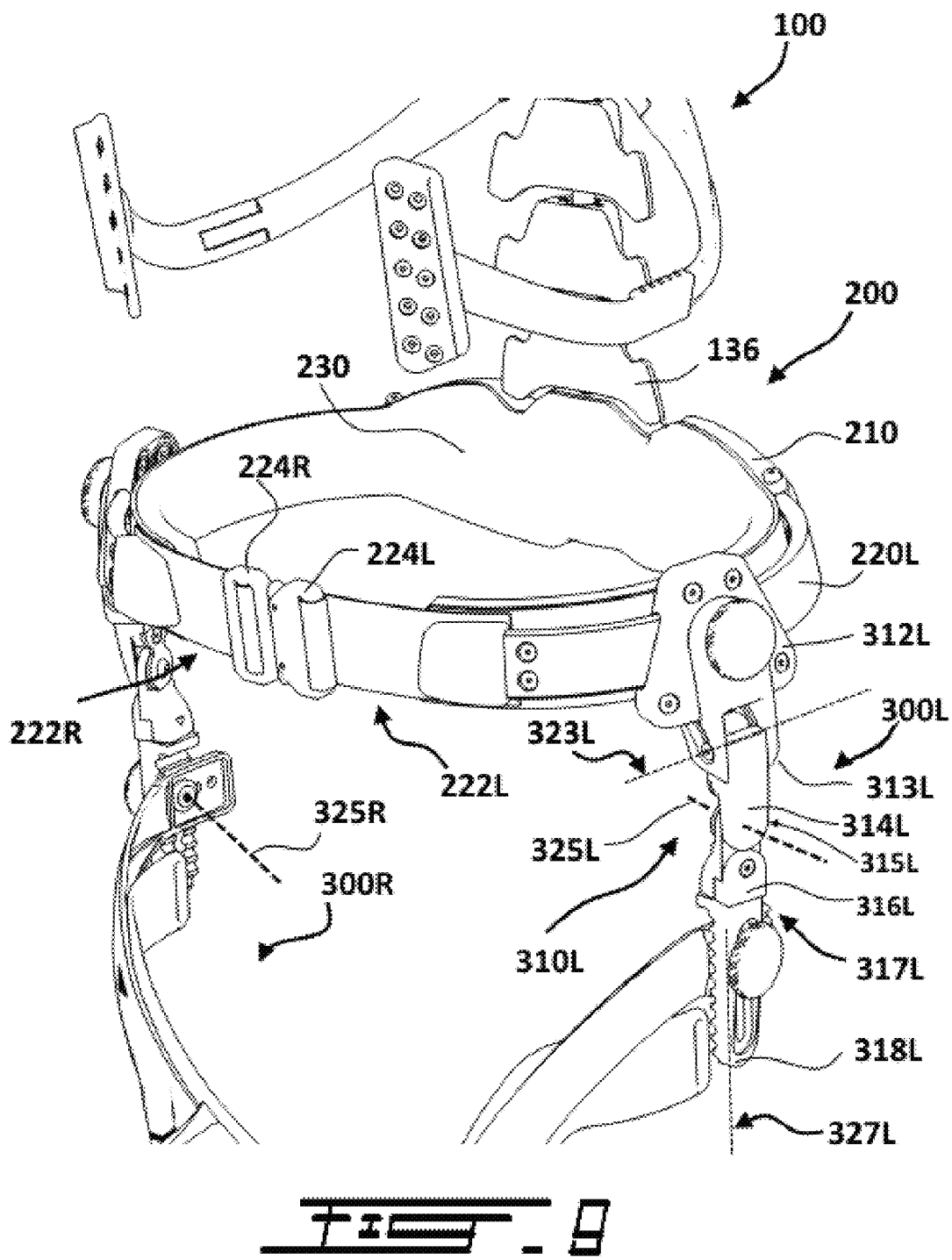
FIG. 9 is a front perspective view of the hip section of the exoskeleton of FIG. 1.
Figure 10:
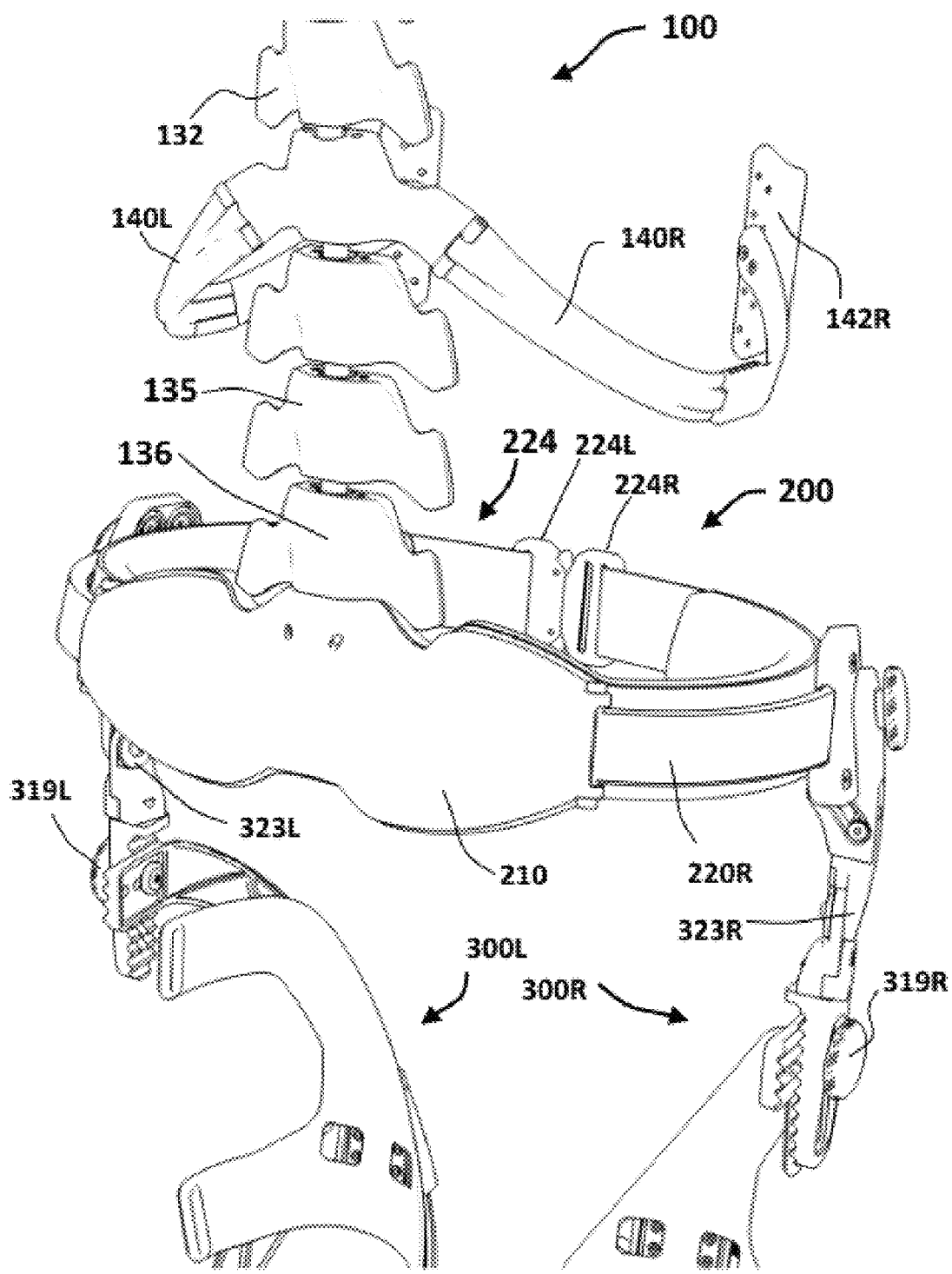
FIG. 10 is a rear perspective view of the hip section of the exoskeleton of FIG. 1.

Referring now to FIGS. 9 and 10, in addition to FIGS. 1 to 6, the hip section 200 is a bridging section between the upper torso section 100 and the lower leg sections 300L and 300R. In that sense, the hip section 200 is generally configured to transfer and redirect the load from the back, where it receives the load from the spine assembly 120, to the sides where it transfers the load to the leg sections 300L and 300R.

In the present embodiment, the hip section 200 comprises a lower back member 210 and two hip members 220L and 220R extending from each side of the lower back member 210 all the way to the front of the user. As best shown in FIG. 9, the free extremities 222L and 222R of the left and right hip members 220L and 220R are provided with complementary fasteners 224L and 224R such as to be attachable together to form a belt (see FIG. 9). In the present embodiment, the complementary fasteners 224L and 224R are buckle members. However, in other embodiments, the complementary fasteners 224L and 224R could be different, for instance, Velcro™ straps.

As shown in FIG. 9 and particularly in FIG. 10, the lower back member 210 is connected to the lowest extremity 124 of the spine assembly 120 of the torso section 100. The connection between the lowest spinal member 136 and the lower back member 210 is similar to the connection between the other spinal members 131 to 136.

As best shown in FIG. 9, when the complementary fasteners 224L and 224R are attached together, the hip section 200 forms a belt which fully circumscribes the hip region of the user. In the present embodiment, for added comfort to the user, the inner surface of the lower back member 210 and of the hip members 220L and 220R is lined with a layer of resilient material such as elastomeric foam 230. Notably, in addition to its role in transferring the load from the torso section 100 to the leg sections 300L and 300R, the hip section 200 also transfers part of the load to the hips of the user, thereby further contributing to alleviating the load carried by the torso of the user. The layer of resilient material therefore generally prevents the hip section 200 to define painful contact points with the hips of the user.

Referring now to FIGS. 9 to 14, to complete the load transfer from the torso down to the ground, the hip section 200 is connected to the pair of left and right leg sections 300L and 300R. Both leg sections 300L and 300R are symmetric in nature, the right leg section 300R being a mirror image of the left leg section 300L. In that sense, only the left leg section 300L will be described below.

The left leg section 300L is fixedly yet adjustably connected to the left hip member 220L of the hip section 200. The left leg section 300L generally comprises three main portions, 1) a hip connector assembly 310L, 2) an upper leg member 330L, and 3) a lower leg member 350L.

Referring to FIGS. 9 and 10, the hip connector assembly 310L is generally responsible to assure the proper connection between the hip section 200 and the left leg section 300L and while allowing the necessary degrees of freedom in the movements of the leg section 300L. In that sense, the hip connector assembly 310L comprises a belt connector 312L, first hip joint member 314L pivotally connected to the belt connector 312L, a second hip joint member 316L pivotally connected to the first hip joint member 314L, and a third hip joint member 318L pivotally connected to the second hip joint member 316L.

As can be seen in FIG. 9, the pivotal connection 313L between the belt connector 312L and first hip joint member 314L defines a first pivot axis 323L which allows for lateral movements (i.e. left-right movements) of the leg of the user. For its part, the pivotal connection 315L between the first hip joint member 314L and second hip joint member 316L defines a second pivot axis 325L which allows for longitudinal movements (i.e. front-rear movements) of the leg of the user. Finally, the pivotal connection 317L between the third hip joint member 318L and the second hip joint member 316L defines a third pivot axis 327L which for axial movements (i.e. rotational movements) of the leg of the user. The three pivot axes 323L, 325L and 327L are generally perpendicular to each other, thereby generally providing three degrees of freedom to the rest of the leg section 300L and thus to the leg of the user. Hence, by providing three degrees of freedom, the hip connector assembly 310L allows the upper and lower leg members 330L and 350L to properly follow the movements of the leg of the user during use.

Figure 11:
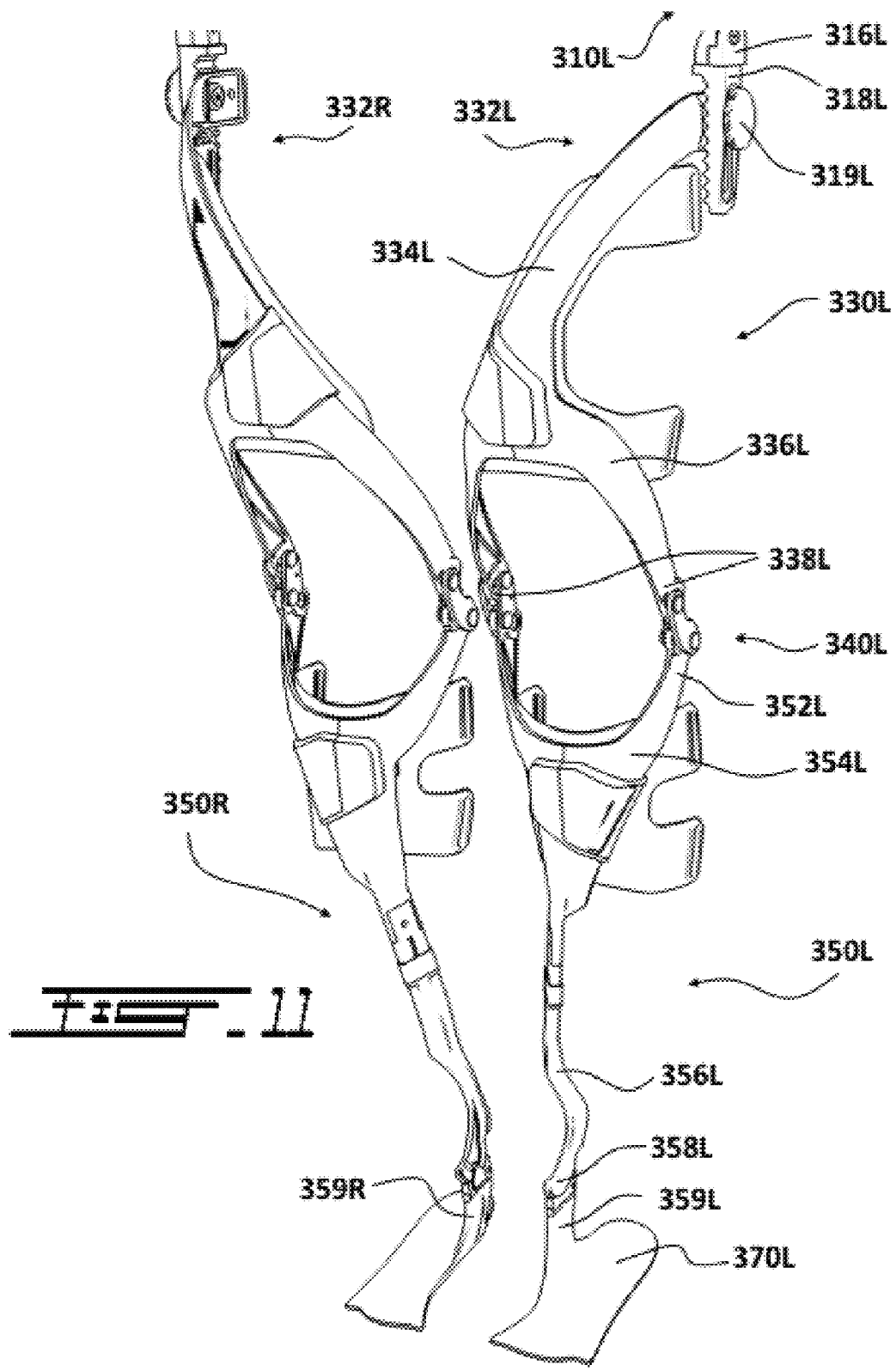
FIG. 11 is a front perspective view of the leg sections of the exoskeleton of FIG. 1.
Figure 12:
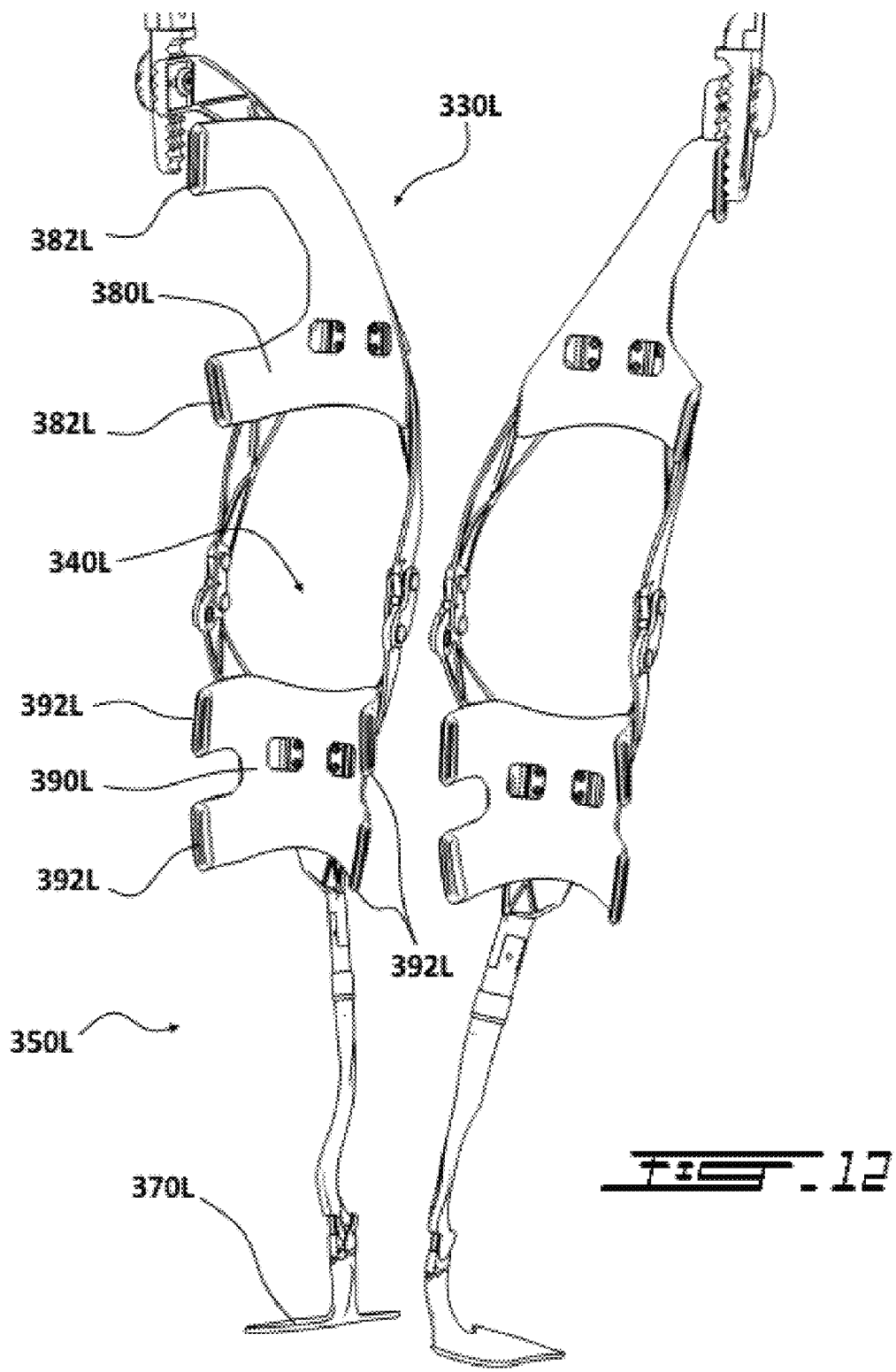
FIG. 12 is a rear perspective view of the leg sections of the exoskeleton of FIG. 1.
Figure 13:
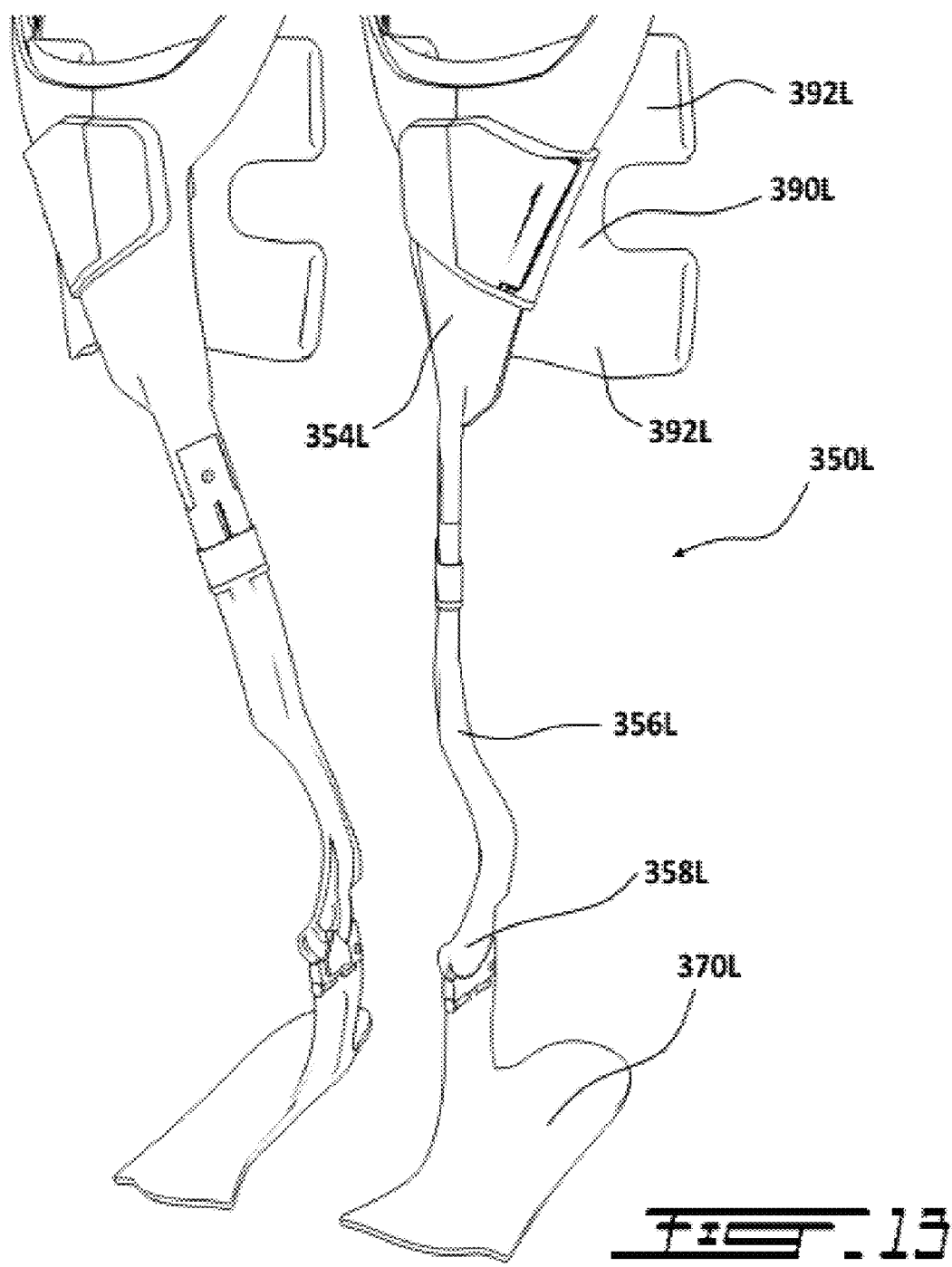
FIG. 13 is a partial front perspective view of the lower portion of the leg sections of the exoskeleton of FIG. 1.
Figure 14:
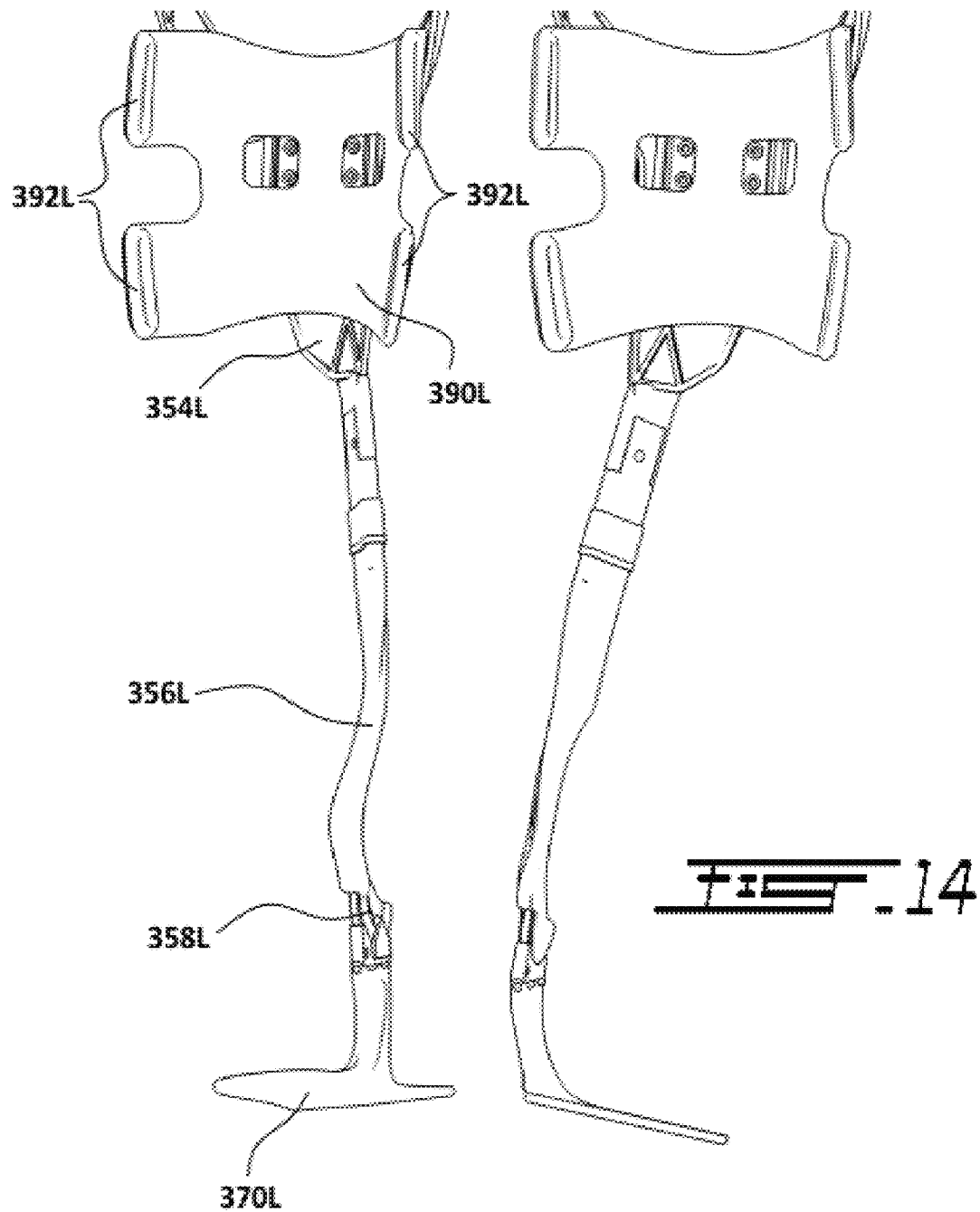
FIG. 14 is a partial rear perspective view of the lower portion of the leg sections of the exoskeleton of FIG. 1.

Referring now to FIGS. 11 and 12, the upper leg member 330L is mounted to the hip joint assembly 310L (see also FIGS. 9 and 10) and generally extends downwardly therefrom. More particularly, the upper extremity 332L of the upper leg member 330L is fixedly yet adjustably connected to the third hip joint member 318L. The adjustable connection 319L between the upper extremity 332L and the third hip joint member 318L generally provides height adjustment to take into account legs of various length.

The upper leg member 330L generally comprises two regions, an upper region 334L and a lower region 336L. As best shown in FIG. 11, the upper region 334L generally extends from the side (e.g. the thigh region) of the user toward the front. Then, extending downwardly from the upper region 334L is the lower region 336L which is terminated near the knee by two extremities 338L as the lower region 336L splits.

For its part, the lower leg member 350L is pivotally connected, at its upper extremities 352L, to the upper leg member 330L, and is terminated at its lower extremity 358L by a sole insert 370L.

As the upper leg member 330L, the lower leg member 350L also comprises an upper region 354L and a lower region 356L extending downwardly therefrom. Notably, as shown in FIG. 11, the upper region 354L of the lower member 350L also splits in two extremities 352L. These two extremities 352L are pivotally connected to the two extremities 352L of the lower region 336L of the upper leg member 330L. The pivotal connected between the extremities 338L and extremities 352L is generally aligned with the knee of the user in order to allow the leg of the user to bend along the knee.

Notably, as shown in FIG. 11 (see also FIG. 3), the split configuration of the extremities 338L and extremities 352L defines a central opening 340L. This opening 340L allows the knee of the user to extend through it when the user kneels or squats.

Reference to FIGS. 11 to 14, the upper region 354L of the lower leg member 350L is generally located at the front of the leg of the user while the lower region 356L extends downwardly and toward the inside of the leg of the user such as to terminate inside the foot of the user. In that sense, the lower region 356L is terminated by a sole insert 370L configured to fit inside the footwear under foot of the user. This sole insert 370L is pivotally connected to the extremity 358L of the lower leg member 350L to allow pivotal movements of the foot of the user.

Referring to FIG. 11 or 12, it will be noted that the leg section 330L transfers the load from the outer side of the leg of the user, near the thigh, all the way down to the inner side of the leg of the user, near the ankle. This load transfer from the outer side of the leg toward the inner side of the leg allows the final load-bearing point to be located inside the foot of the user in accordance with the biomechanics of the human body. In that sense, since the inner side of the foot is better configured to support load, transferring the load on the inner side of the foot can prevent injuries to the user of the exoskeleton 10.

Referring to FIGS. 11-14, when a user is standing straight, walking or running, the leg remains in its normal circumference and geometry. Upon kneeling on one leg, two legs, or adopting a crouching position, the circumference of the leg typically increases within a range varying between none to several inches, depending on the age and ethnic background of the individual. This situation applies specifically to the thigh and the calves region of the legs.

Referring to FIGS. 18-21, in the present embodiment, section A (dark grey: thigh extender which is connected to the knee pivot joint, which is in turn connected to the tibia extender) generally moves horizontally towards the inner side of the leg by the expansion of the muscles when the user adopts a lower position as described above while Section B (light grey: knee/thigh/tibia mechanism) generally remains fixed and does not move.

Figure 20:
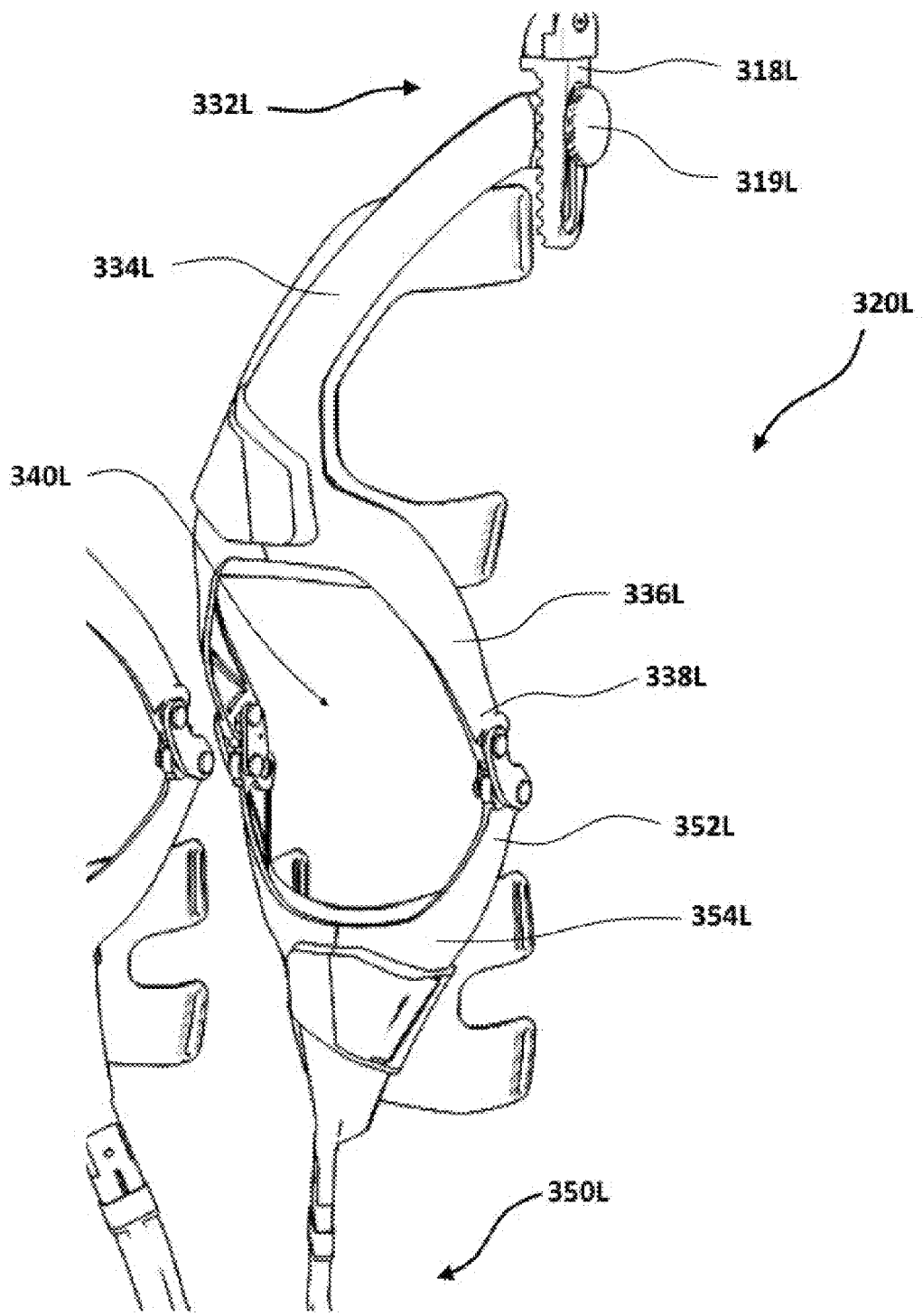
FIG. 20 is a front perspective view of the leg sections of the exoskeleton of FIG. 1.
Figure 21:
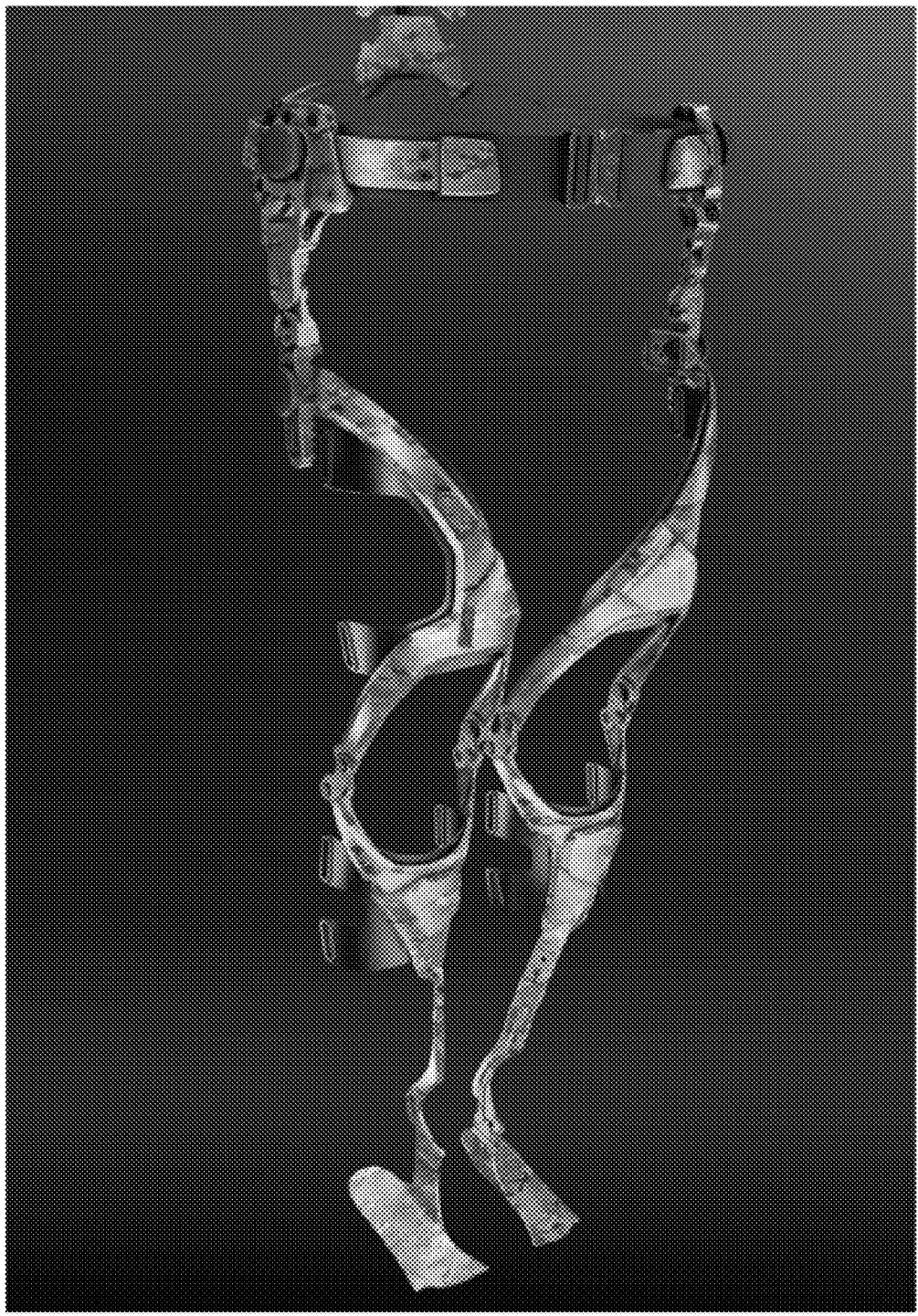
FIG. 21 is a front perspective view of the lower body sections of the exoskeleton of FIG. 1.

Referring to FIG. 20, elements 334, 336 and 354 preferably remain fixed and do not move, as opposed to symmetrical counterpart elements of the inner side which typically shifts horizontally towards the inner side of the leg by the expansion of the muscles when the user adopts a lower position as described above.

Referring now to FIG. 12 (see also FIG. 4), the back of both the upper leg member 330L and lower leg member 350L is provided with strap attachment extensions 380L and 390L each comprises attachment loops 382L and 392L.

These loops 382L and 392L are configured to receive attachment straps (not shown) to secure the leg section 330L to the leg of the user. Typically, the straps are elastic and/or adjustable strap to provide proper attachment between the leg section 330L and the leg of the user.

Also, as for the hip section 200, the rear surface of the leg sections 380L and 390L could be provided with a layer of resilient material such as elastomeric foam for added comfort.

Figure 17:
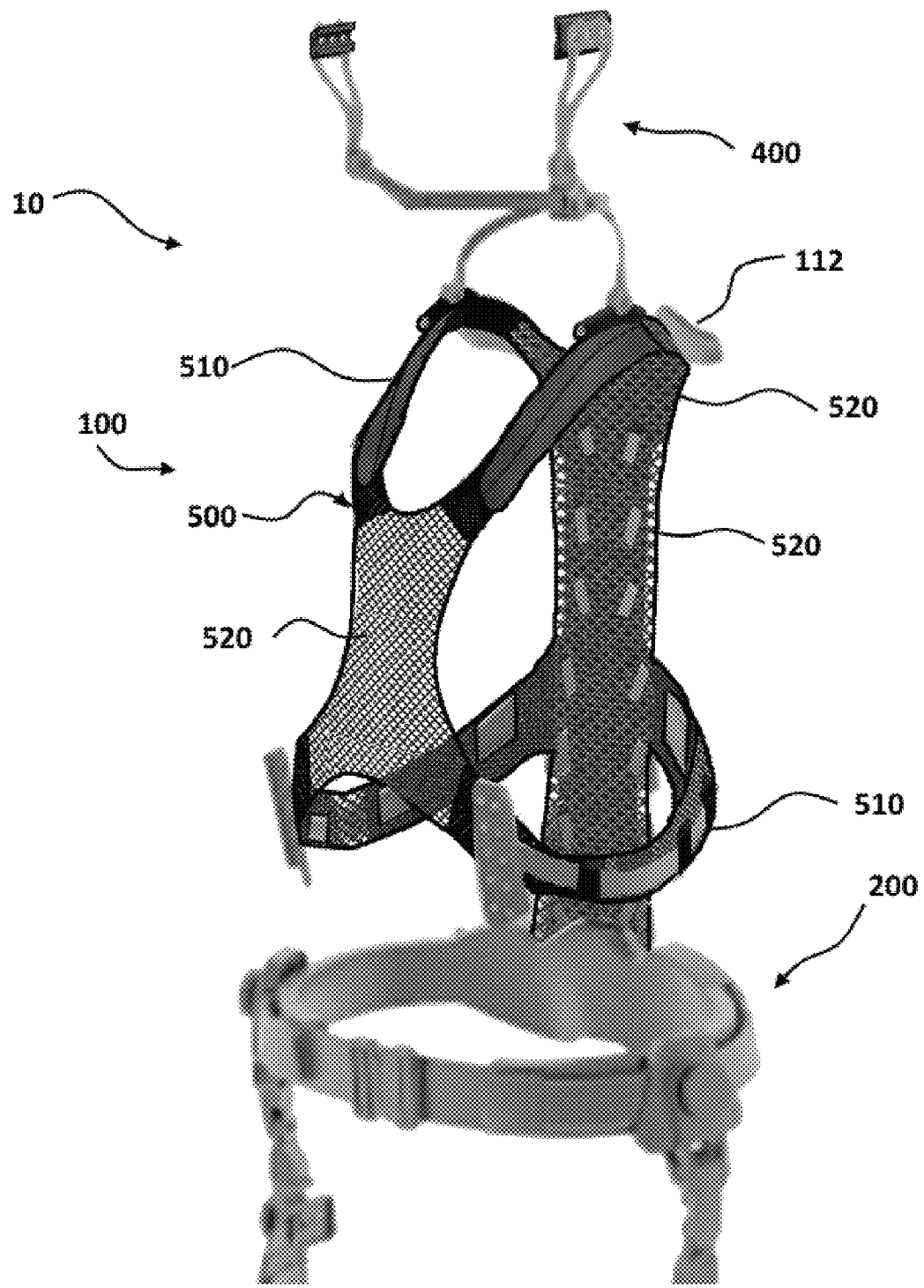
FIG. 17 is a front perspective view of the exoskeleton of FIG. 1, further showing a covering vest.
Figure 18:
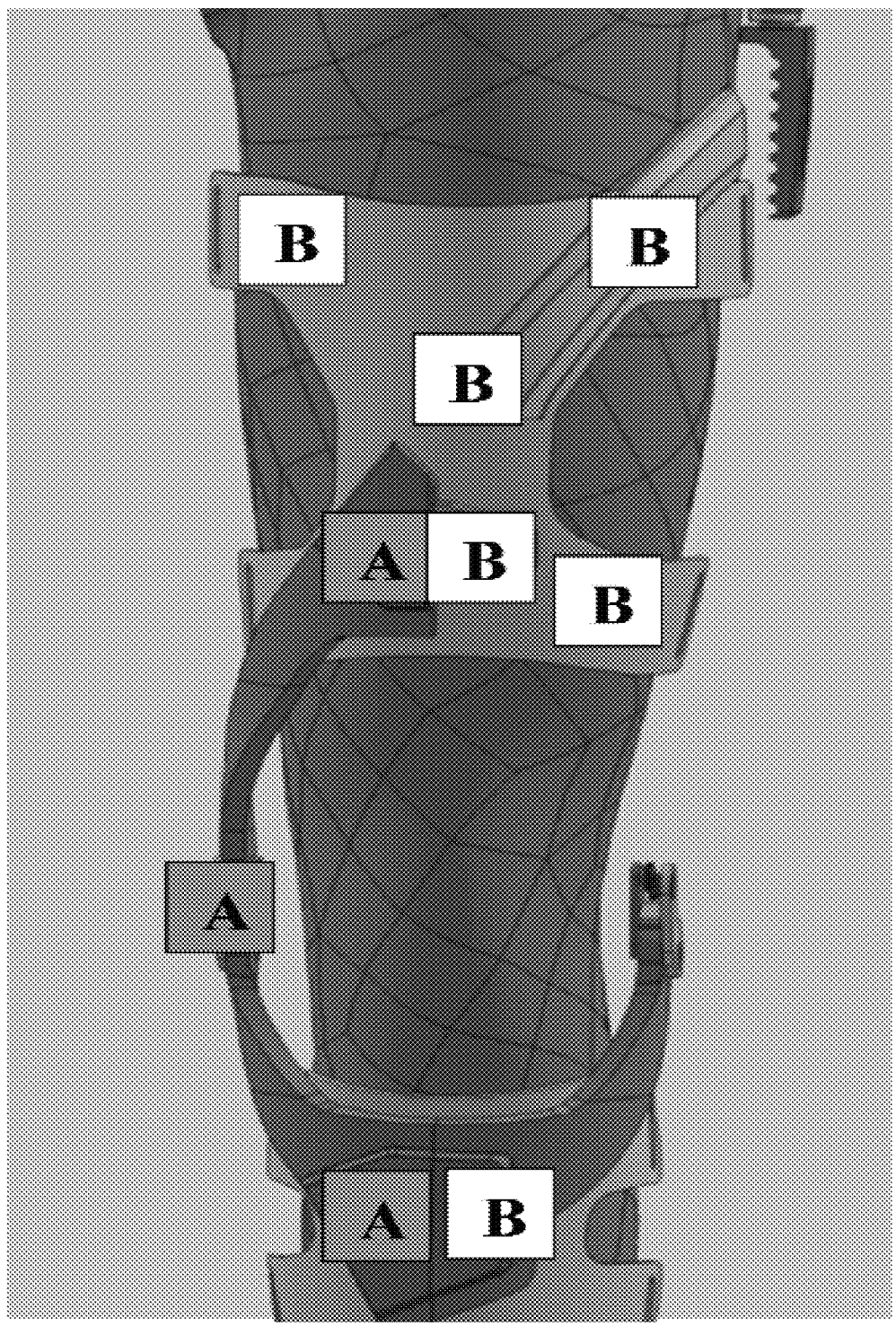
FIG. 18 is a front view of the leg section of the exoskeleton of FIG. 1.
Figure 19:
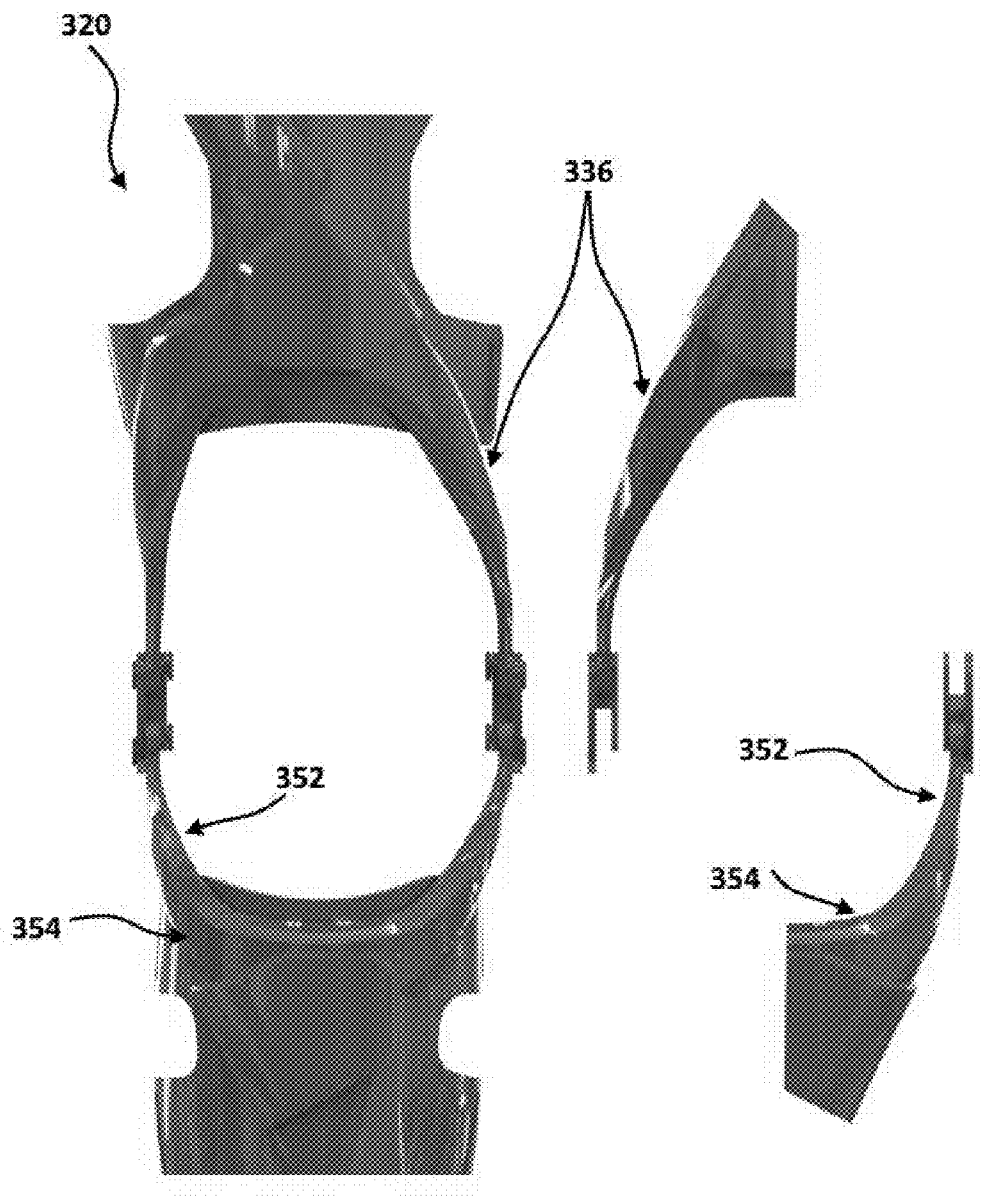
FIG. 19 is a front view of the leg sections of the exoskeleton of FIG. 1.

As mentioned above, the present embodiment of the exoskeleton 10 also comprises a neck section 400 which is generally configured to transfer the load generated by a helmet (not shown) down to the torso section 100. As shown in FIG. 17, in the present embodiment, the neck section 400 is connected to the torso section 100 via a vest 500. The vest 500 is generally integrated with the torso section 100 such as to allow the vest 500 to secure the torso section 100 to the torso of the user. In the present embodiment, the vest 500 is made from padded straps 510 and mesh 520.

Figure 15:
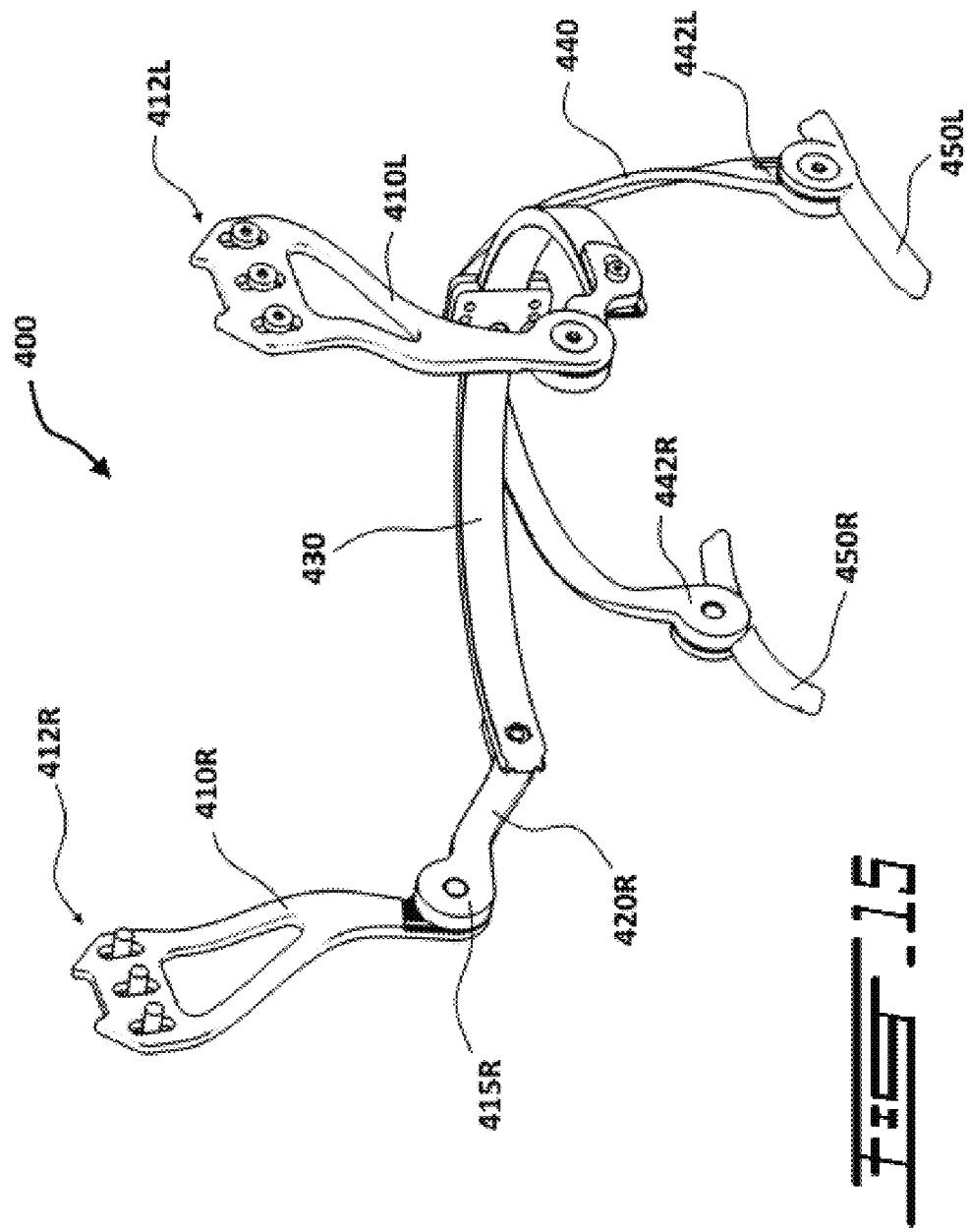
FIG. 15 is a front perspective view of the neck section of the exoskeleton of FIG. 1.
Figure 16:
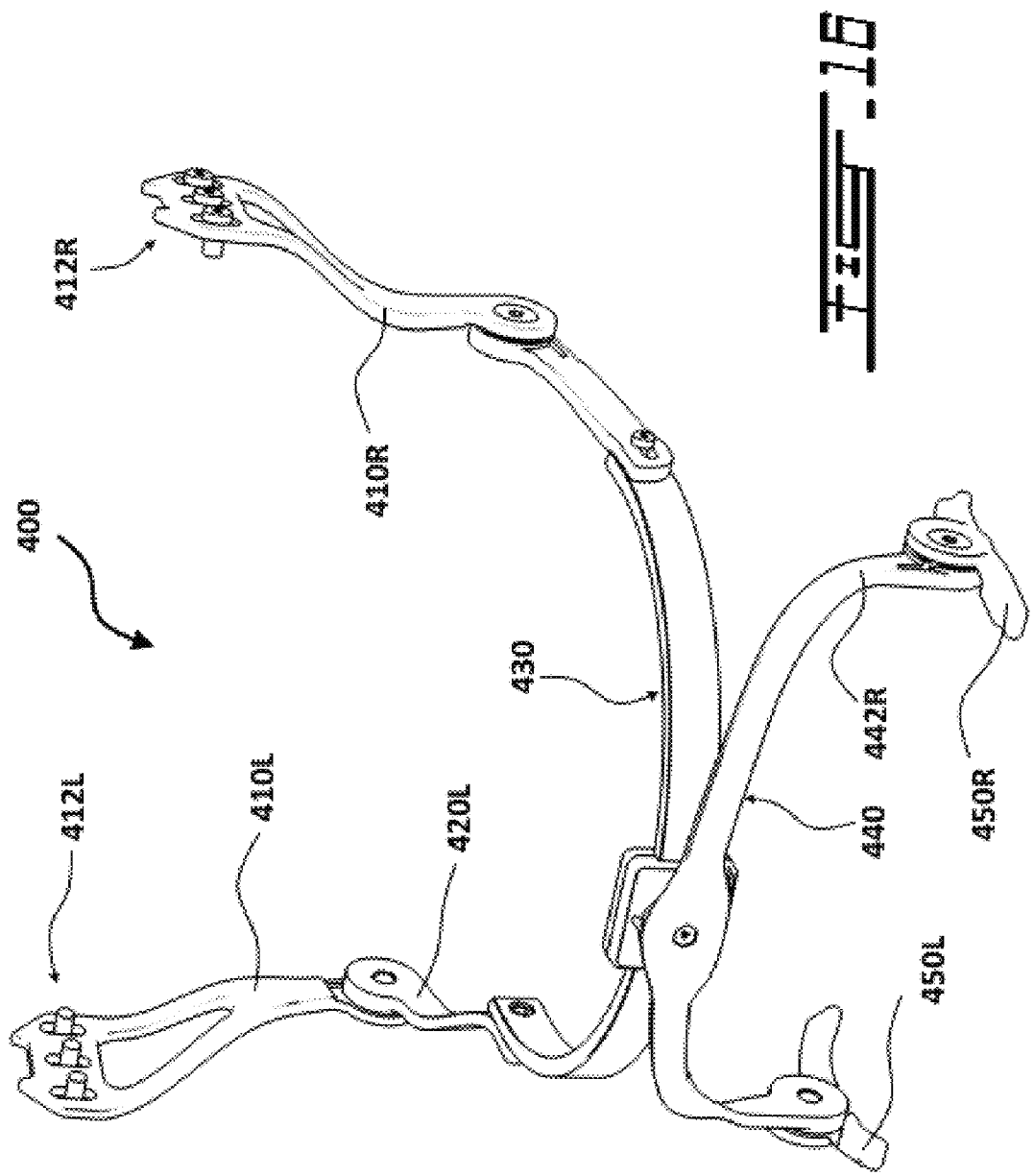
FIG. 16 is a rear perspective view of the neck section of the exoskeleton of FIG. 1.

Referring to FIGS. 15 and 16, to allow the neck section 400 to properly transfer the load of the helmet down to the torso section 100, the neck section 400 comprises a pair of left and right helmet support members 410L and 410R which are configured to be mounted to the helmet via attachment points 412L and 412R, and which are pivotally connected to first neck members 420L and 420R. These two first neck members 420L and 420R are further connected to second neck member 430 which is shaped to extend along the rear of the head of the user. This second neck member 430 is further connected to a third neck member 440 which extends downwardly toward the shoulders of the user. In that sense, the lower extremities 442L and 442R of the third neck member 440 are provided with vest attachment members 450L and 450R pivotally attached thereto.

In operation, trajectory of the static and dynamic loads along the exoskeleton 10 is as follows.

In the present embodiment, in operation, when the person is standing, walking, or running this exoskeleton system 10 takes the load which is typically on the torso, lifts it away from the body and redirects it to the floor underneath the foot (i.e. the load is now redirected strategically to the area where the bipedal body manages better the load).

While standing, walking, or running, the trajectory of the static and dynamic loads involved is as followed:
- I. The load of the helmet is typically taken off the neck and redirected down to the shoulders via the transfer mechanisms 412, 415, 430, 442 (see FIG. 15).
- II. From I, the load is lifted from underneath the shoulders by the load-lifter wing transfer mechanism 112 (see FIGS. 5-7).
- III. From II, it flows through the vertebrae 110, 131 to 136 (see FIG. 8) of the artificial spine to reach the hip area 230 (see FIG. 9). Hence, the load is typically on the outside of the body, just over the hip.
- IV. From III, it continues through the hip area via the slider/connector/junctions 319, 323, 312 (see FIG. 10) all the way down to the legs.
- V. From IV, it continues through the knee area 319, 354, 356 (see FIG. 11).
- VI. From V, the load is redirected to the inside of the leg via transfer mechanisms 356, 358, 359 (see FIG. 11).
- VII. From VI, the load takes a trajectory describing a 0 to 90 degree (from vertical to horizontal direction—lower interior side of the tibia towards the big toe) before finally reaching underneath the foot 370 (see FIG. 11).

In the present embodiment, now referring to FIGS. 22-25, in operation, at certain positions, the functioning of the vertebrae 131 to 136 of the vertebrae assembly (artificial spine) is preferably a self-adjustable dynamic load transfer mechanism designed specifically for the human spine.

In the present embodiment, the vertebrae assembly 600 is composed of several individual device-parts identified as vertebrae which are characterized in 4 types: Lumbar Vertebrae (134 to 136), Rib Shock Vertebra 133 (which extends into the Rib Shock assembly connection (140 to 144)), Thoracic Vertebrae 131-132 and Upper Vertebra 110 (which extends into the Load-lifter wings 112).

Figure 22:
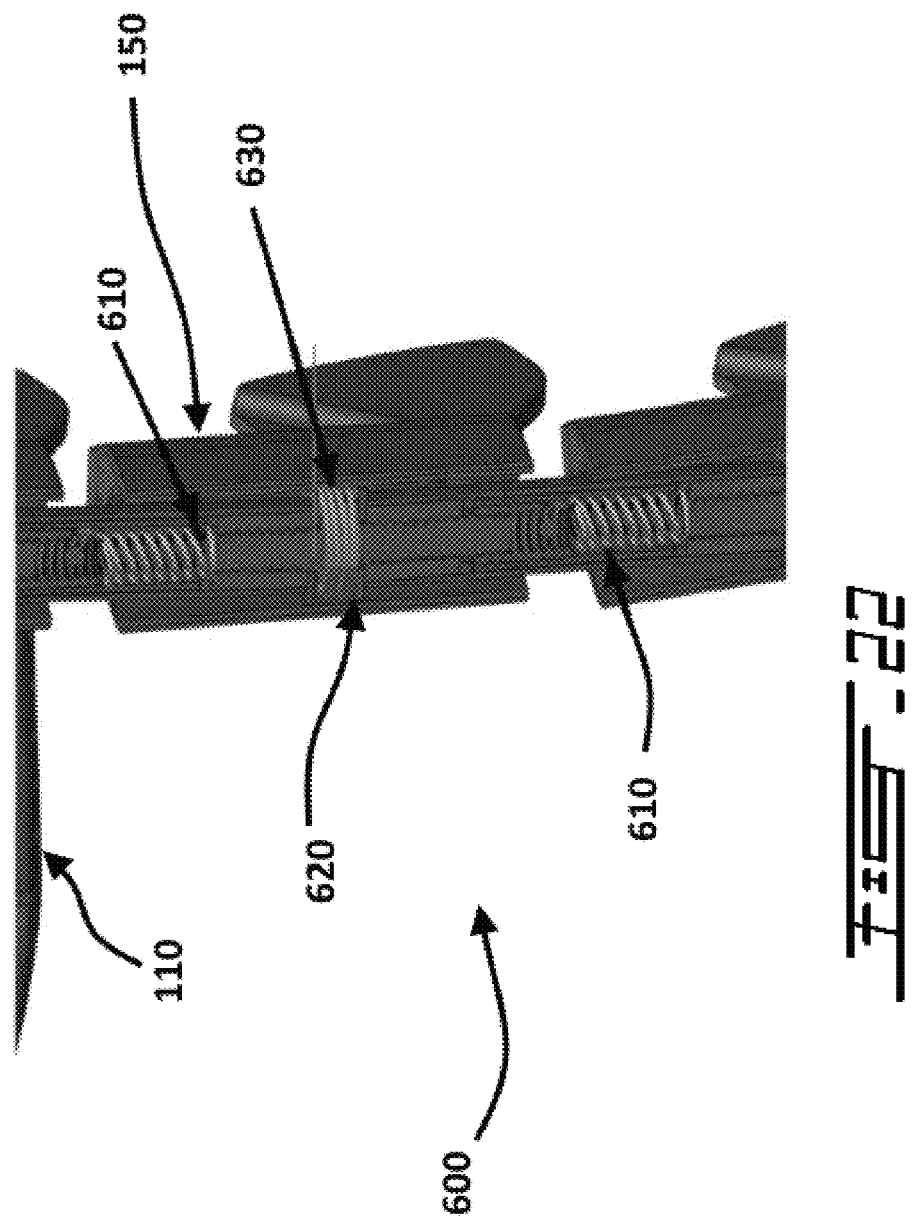
FIG. 22 is a schematic view of the vertebrae section of the exoskeleton of FIG. 1.

Referring to FIG. 22, the vertebrae assembly 600 comprises telescopic internal springs 610, inter-vertebrae springs 620, and spherical contact load transfer 630.

Each one of these vertebrae (110, 131 to 136) preferably moves freely in relation to others on 4 axis: rotation, flexion, lateral flexion and translation. The upper vertebra (110) is typically the device-part that has the capacity to handle the load. The functioning of this vertebrae assembly with regards to the global system sustaining a certain charge depends on the specific posture/activities/positions as well as transfer mechanisms described below:

Standing Straight, Walking, Running and Prone Position

Figure 23:
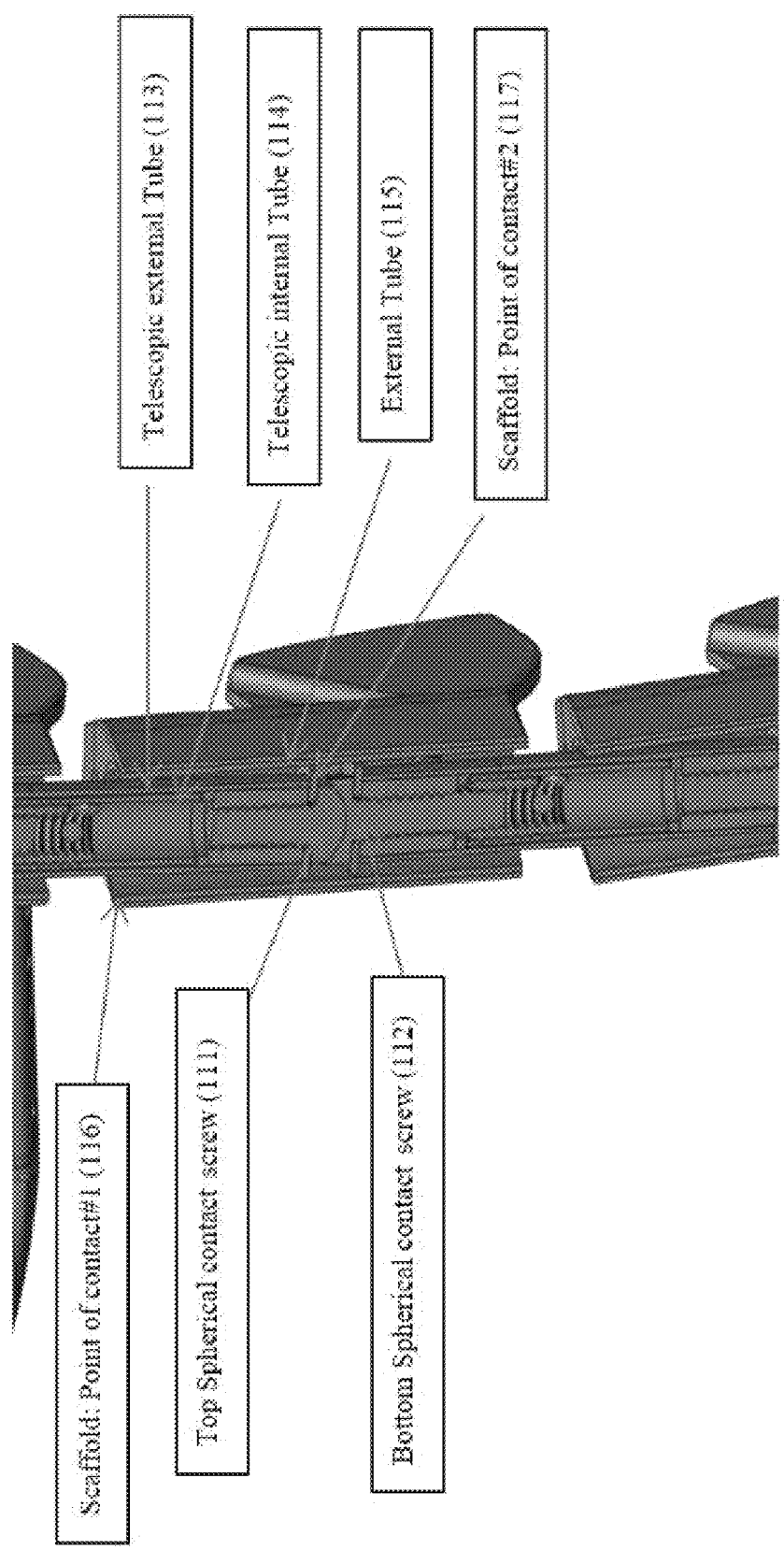
FIG. 23 is a schematic view of the vertebrae section of the exoskeleton of FIG. 1.
Figure 24:
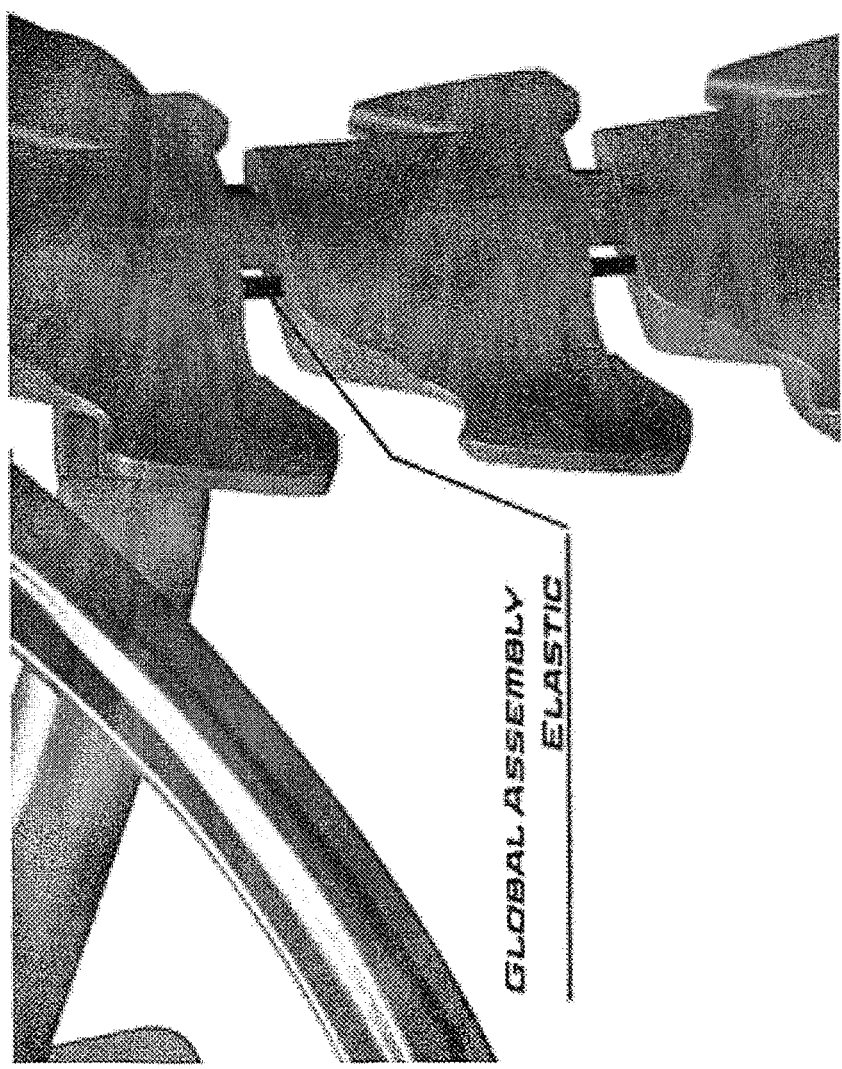
FIG. 24 is a schematic view of the vertebrae section of the exoskeleton of FIG. 1.
Figure 25:
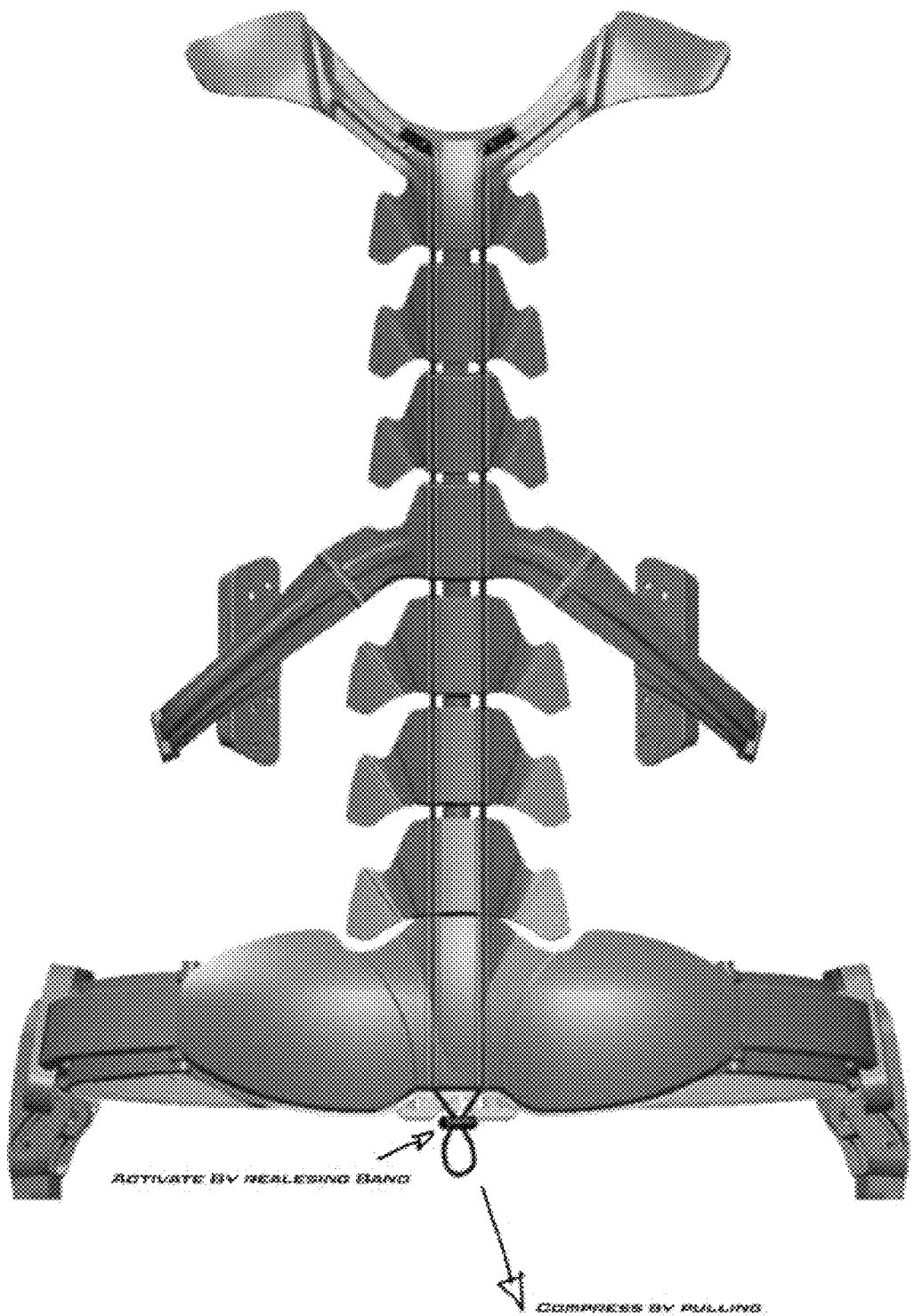
FIG. 25 is a rear view of the torso sections of the exoskeleton of FIG. 1.

In the present embodiment, referring to FIG. 23, while standing straight all vertebrae (110, 131 to 136) (see FIG. 8) from the assembly are directly in contact trough the spherical contact surface 111, 112 at the extremity of each vertebra.

While walking and running, the load will still be transmitted through this direct contact. Also if a limited leaning motion is performed (less than 10 degrees) on any side, the vertebrae assembly will still transfer the load (or translate) through direct contact.

Leaning on any Side and Kneeling

Once the movement of the user reaches a more than 10 degree-leaning motion, the spine typically extends following a certain pattern: lumbar section translates more than the other sections; the other sections translate in a similar way.

Referring to FIG. 23, when the spine extends, it generally creates a translation between each vertebra points of contact 111, 112 which disconnects the spherical surface contact that is supporting the load in straight position. To continue transferring the load the assembly uses the inner tube contact inside the vertebrae 115. It's the two contacts created by the scaffold points of contact 111, 112 and 116, 117 that now transfers the load. This mechanism is identified as the scaffold.

Still referring to FIG. 23, as the scaffold mechanism increases, a larger angle of flexibility is obtained between the vertebrae 131 to 136 (see FIG. 8); so the more there is a leaning motion, the more the translation between vertebrae 131 to 136 (see FIG. 8) increases, and the more flexible they become. The lumbar vertebrae translate so much that a telescopic mechanism 113, 114 has been incorporated inside them to compensate excessive translation that occurs in a 'kneeling' position. To ensure proper functioning of the whole system, the device-parts of the vertebrae assembly need to hold together adequately on the user. Therefore, springs, elastics, and textile retainers are inherently integrated to the design of this vertebrae assembly.

Springs, Elastics and Textile Retainers

A spring is inserted inside each vertebra 131 to 136 (see FIG. 8); this spring pushes the other vertebrae 131 to 136 (see FIG. 8) apart (see FIG. 22). A specific spring is inserted into the lumbar section to activate the telescopic mechanism of the Lumbar vertebrae (see FIG. 22). The global assembly is then tightened by an elastic that pulls the whole vertebrae assembly together (see FIGS. 24-25).

Self-Adjustable

This mechanism is preferably self-adjustable in a way that moving with the load on the shoulder is rendered effortless.

Upon movement of the user, a slight offset (from the center of the body) of the position of the load vector is triggered; this offset generally engages the vertebrae 131 to 136 (see FIG. 8) which pull the whole system (body+exoskeleton) into the direction of the movement.

The load carried by the user on its chest, shoulders and/or back is at least partially supported by the shoulder member 110 and spine assembly 120 of the torso section 100. The load is thus directed toward the back and along the spine assembly 120 which further directs it down to the hip section 200. The hip section 200 splits the load in two as it redirects it to the left and right hip members 220L and 220R. The left and right hip members 220L and 220R further redirect the load down the left and right leg sections 300L and 300R respectively. The leg sections 300L and 300R then redirect the load from the outside of the legs toward the inside of the legs such as to finally contact the ground near the inside of the feet of the user.

Hence, when the user wearing the exoskeleton 10 is standing, walking, running, kneeling, squatting, etc., this exoskeleton 10 takes at least part of the load which is on the torso of the user, lifts it away from the body and redirects it toward the ground underneath the feet of the user.

Typically, the exoskeleton 10 is generally made of titanium or other lightweight alloy. Still, the exoskeleton 10 could have some of its components made of composite material, such as carbon fiber or aramid and/or a combination of both, the articulations and the vertebrae remaining however in titanium. In order to reduce the weight further, the titanium could be made of a sparse material (i.e. metallic alloy comprising embedded gas bubbles).

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. An exoskeleton configured to be worn by a use to support and transfer a load carried by the user; the exoskeleton comprising a torso section connected to a leg section via a hip section such as to transfer the load carried by the torso section down to the ground via the hip section and then the leg section; wherein the leg section comprises two symmetrical articulated leg assemblies, each leg assembly being adapted to be maintained on each user's leg and to follow the leg's movements when the exoskeleton is in use, each leg assembly having an upper end operatively connected to an outer side of the hip section and a bottom end adapted to be in contact with the ground, each leg assembly being configured to transfer the load from the outer side of the hip section to an inner side of the user's leg;

wherein each leg assembly comprises:

an upper leg member extending downwardly from the hip section and having an end pivotally connected to the hip section to allow the upper leg member to move with respect to the hip section when the user moves; and a lower leg member extending downwardly from the upper leg member and pivotally connected to the upper leg member, the pivotal connection between the upper and lower leg members being located at a knee level of the user to allow the lower leg member to follow the movements of the lower leg of the user with respect to the upper leg;

the upper and lower leg members extending downwardly and toward the inner side of the user's leg such as to transfer the load from the outside of the leg toward the inside of the leg and down on the inner side of the foot of the user; and wherein the upper leg member comprises an upper region extending downwardly from the outer side of the hip section toward a front of the leg, and then extending downwardly from the upper region to a lower region terminated near the knee level by two extremities as the lower region splits on each side of the leg; and the lower leg member comprises an upper region pivotally extending from the lower region of the upper leg member and a lower region extending downwardly therefrom toward the inner side of the user's leg, the upper region of the lower member also splits in two extremities which are each pivotally connected to the two extremities of the lower region of the upper leg member defining as such a central opening to allow the knee of the user to extend through said opening when the user kneels or squats;

the pivotal connection between the said extremities being aligned with the knee of the user in order to allow the leg of the user to bend along the knee.

2. The exoskeleton of claim 1, wherein each leg assembly further comprises a hip joint assembly for operatively connecting the upper leg member to the hip section, the hip joint assembly being articulated for transferring the user's movement between the hip and leg sections, the hip joint assembly also comprising an adjusting system for adjusting a length of the leg assembly with a length of the user's leg.

3. The exoskeleton of claim 2, wherein the hip joint assembly comprises:
a belt connector to connect the hip joint assembly to the outer side of the hip section,
a first hip joint member pivotally connected to the belt connector such as to form a first pivotal connection,
a second hip joint member pivotally connected to the first hip joint member such as to form a second pivotal connection, and
a third hip joint member pivotally connected to the second hip joint member such as to form a third pivotal connection; and wherein:
the first pivotal connection between the belt connector and first hip joint member defines a first pivot axis which allows for lateral or left-right movements of the leg of the user,
the second pivotal connection between the first hip joint member and second hip joint member defines a second pivot axis which allows for longitudinal or front-rear movements of the leg of the user, and
the third pivotal connection between the third hip joint member and the second hip joint member defines a third pivot axis which allows for axial or rotational movements of the leg of the user;
the three pivot axis being perpendicular to each other, thereby generally providing three degrees of freedom to the leg section providing as such movements of the leg of the user during use.

4. The exoskeleton of claim 1, wherein the lower leg member is terminated with a sole insert extending outwardly from the lower leg member and adapted to be received inside or outside a user's footwear.

5. The exoskeleton of claim 1, wherein the torso section of the exoskeleton comprises:
a shoulder member configured to rest on the shoulders of the user; and
a spine assembly extending downwardly from the shoulder member along the user's spine and comprising a plurality of spinal members wherein an uppermost spinal member is connected to, or integral with, the shoulder member, while a lowermost spinal member is connected to the hip section;
the torso section supporting and transferring the load carried by the shoulders and torso of the user toward the ground via the hip section and then the leg section.

6. The exoskeleton of claim 5, wherein the shoulder and spinal members are interconnected by resilient members to allow the spine assembly to compress or extend under load and to allow the spine assembly to relatively follow the movements of the user's torso.

7. The exoskeleton of claim 6, wherein the spinal members of the spine assembly are interconnected using telescopic internal springs, inter-vertebrae springs, and/or spherical contact load transfer.

8. The exoskeleton of claim 5, wherein the torso section also comprises at least one pair of left and right rib members which extend on each side of at least one intermediate spinal member all the way to the front of the torso of the user at the level of the user's lowest ribs, between the thorax and abdomen, for supporting and transferring the load carried by the thorax or abdomen toward the spinal assembly and then toward the ground via the hip and leg sections.

9. The exoskeleton of claim 1, wherein the hip section comprises a lower back member connected to the torso section and left and right hip members extending from each side of the lower back member all the way to the front of the user, the left and right hip members having extremities provided with complementary fasteners such as to be attachable together to form a belt.

10. The exoskeleton of claim 1, wherein the exoskeleton further comprises a neck section configured to assist in supporting the load carried by the head of the user, the neck section being removably connected to the torso section such as to transfer the load from the head and neck of the user toward the torso section which will further transfer the load down to the ground via the hip and leg sections.

11. The exoskeleton of claim 10, wherein the neck section is connected to the torso section via a vest integrated with the torso section such as to allow the vest to secure the torso section to the torso of the user.

12. The exoskeleton of claim 10, wherein the neck section is adapted to be connected to a helmet worn by the user to protect his head and/or to support the load to be carried by the user.

13. The exoskeleton of claim 1, wherein the exoskeleton further comprises one or more resilient pads affixed between the exoskeleton and the user for adding comfort when the user is wearing the exoskeleton.

14. The exoskeleton of claim 1, further comprising a vest adaptable to a size of the user's torso for securing the torso section to the user's torso.

15. The exoskeleton of claim 1, further comprising a plurality of fastening assemblies for fastening the exoskeleton to the user.

16. The exoskeleton of claim 1, wherein the exoskeleton is a passive exoskeleton.

17. An exoskeleton configured to be worn by a user to support and transfer a load carried by the user; the exoskeleton comprising a torso section connected to a leg section via a hip section such as to transfer the load carried by the torso section down to the ground via the hip section and then the leg section; wherein the leg section comprises two symmetrical articulated leg assemblies, each leg assembly being adapted to be maintained on each user's leg and to follow the leg's movements when the exoskeleton is in use, each leg assembly having an upper end operatively connected to an outer side of the hip section and a bottom end adapted to be in contact with the ground, each leg assembly being configured to transfer the load from the outer side of the hip section to an inner side of the user's leg;

wherein the torso section of the exoskeleton comprises:
  a shoulder member configured to rest on the shoulders of the user; and
  a spine assembly extending downwardly from the shoulder member along the user's spine and comprising a plurality of spinal members wherein an uppermost spinal member is connected to, or integral with, the shoulder member, while a lowermost spinal member is connected to the hip section;

wherein each leg assembly comprises:
  an upper leg member extending downwardly from the hip section and having an end pivotally connected to the hip section to allow the upper leg member to move with respect to the hip section when the user moves; and
  a lower leg member extending downwardly from the upper leg member and pivotally connected to the upper leg member, the pivotal connection between the upper and lower leg members being located at a knee level of the user to allow the lower leg member to follow the movements of the lower leg of the user with respect to the upper leg;
  the upper and lower leg members extending downwardly and toward the inner side of the user's leg such as to transfer the load from the outside of the leg toward the inside of the leg and down on the inner side of the foot of the user.

18. The exoskeleton of claim 17, wherein each leg assembly further comprises a hip joint assembly for operatively connecting the upper leg member to the hip section, the hip joint assembly being articulated for transferring the user's movement between the hip and leg sections, the hip joint assembly also comprising an adjusting system for adjusting a length of the leg assembly with a length of the user's leg.

19. The exoskeleton of claim 17, wherein the lower leg member is terminated with a sole insert extending outwardly from the lower leg member and adapted to be received inside or outside a user's footwear.

20. The exoskeleton of claim 17, wherein the exoskeleton further comprises a neck section configured to assist in supporting the load carried by the head of the user, the neck section being removably connected to the torso section such as to transfer the load from the head and neck of the user toward the torso section which will further transfer the load down to the ground via the hip and leg sections; the neck section being connected to the torso section via a vest integrated with the torso section such as to allow the vest to secure the torso section to the torso of the user.

* * * * *